(12) United States Patent
Frolov et al.

(10) Patent No.: US 7,332,322 B2
(45) Date of Patent: Feb. 19, 2008

(54) VENEZUELAN EQUINE ENCEPHALITIS VIRUS REPLICONS WITH ADAPTIVE MUTATIONS IN THE GENOME AND USES THEREOF

(76) Inventors: Ilya Frolov, 41 Lakeview Dr., Galveston, TX (US) 77551; Elena Frolova, 41 Lakeview Dr., Galveston, TX (US) 77551

( * ) Notice: Subject to any disclaimer, the term of this patent is extended or adjusted under 35 U.S.C. 154(b) by 0 days.

(21) Appl. No.: 11/227,671

(22) Filed: Sep. 14, 2005

(65) Prior Publication Data

US 2006/0251678 A1 Nov. 9, 2006

Related U.S. Application Data

(60) Provisional application No. 60/609,800, filed on Sep. 14, 2004, now abandoned.

(51) Int. Cl.
*C12N 7/04* (2006.01)
*C12N 15/86* (2006.01)
*C12P 21/04* (2006.01)
*C12P 19/34* (2006.01)
*C12Q 1/68* (2006.01)

(52) U.S. Cl. .............. 435/236; 435/5; 435/6; 435/71.1; 435/91.1; 435/456

(58) Field of Classification Search ...... None
See application file for complete search history.

(56) References Cited

U.S. PATENT DOCUMENTS

2003/0119182 A1* 6/2003 Smith et al. ............. 435/320.1

OTHER PUBLICATIONS

White et al., Role of Alpha/Beta Interferon in Venezuelan Equine Encephalitis Virus Pathogenisis: Effect of an Attenuating Mutation in the 5' Untranslated Region, Journal of Virology, Apr. 2001, vol. 75, No. 8, pp. 3706-3718.*

* cited by examiner

*Primary Examiner*—Bruce R. Campell
*Assistant Examiner*—Sharon Hurt
(74) *Attorney, Agent, or Firm*—Benjamin Aaron Adler

(57) ABSTRACT

The present invention provides a Venezuelan equine encephalitis virus replicon RNA useful in the development of stable lines of mammalian, avian and insect cells in which these replicons will persistently replicate. Venezuelan equine encephalitis (VEE) virus replicons contain a number of unique adaptive mutations that make the replicons non-cytopathic. The replicons remain resistant to IFN-α/β. Replicon replication leads to high-level production of heterologous proteins, which are encoded by the replicons' genome and are under the control of a viral subgenomic promoter. Also provided are methods of screening for inhibitory compounds of Venezuelan equine encephalitis virus replication and eastern equine encephalitis virus replication.

15 Claims, 21 Drawing Sheets

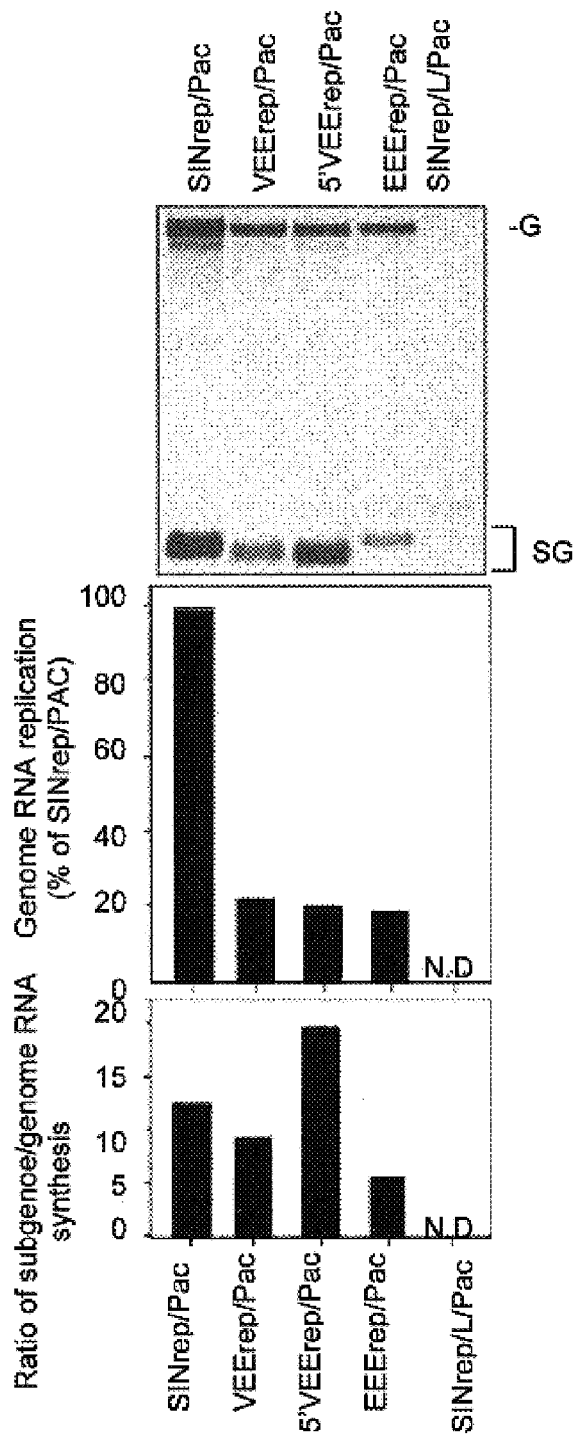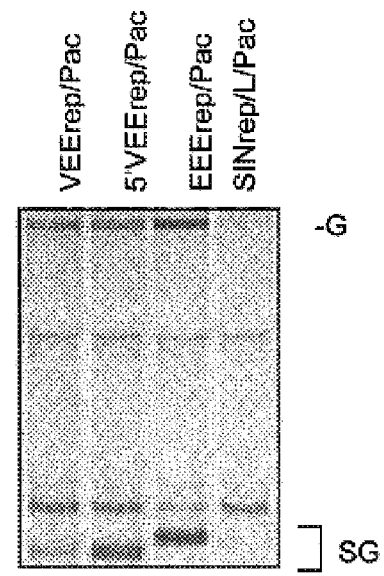
Fig. 2A
Fig. 2B

```
                  L
                  T
              P   S                                    L
VEE   707   ACLHLNPGGTCVSIGYGYADRASESIIGAIARQFKFSRVCKPKSSLEE
EEE         -VD---K----IAL---T----T-N--S-V--S-R-----Q--CAW-N
SIN         -LNC-------L-VKS------N--DVVT-L--K-VRVSAAR-DCVSSN
SFV         -LRL-K---*ILMRA-----KI--AVVSSLS-K-SSA--LR-DCVTSN

K      S
VEE         TEVLFVFIGYD*RKARTHNPYK   775    (SEQ ID NO: 3)
EEE         ---A---F-K-NGNHLQDQDRL          (SEQ ID NO: 4)
SIN         --NYLI-RQL-NSRT-QFT-HH          (SEQ ID NO: 5)
SFV         ---FLL-SNF-NG-*-PSTLHQ          (SEQ ID NO: 6)
```

Fig. 7A

```
                           P
VEE   108   LLSTGIFSGNKDRLTQSLNHLLT   130    (SEQ ID NO: 7)
EEE         ------YA-G---VM------F-          (SEQ ID NO: 8)
SIN         ------YAAG----EV---C-T-          (SEQ ID NO: 9)
SFV         -----V---GR---Q------F-          (SEQ ID NO: 10)
```

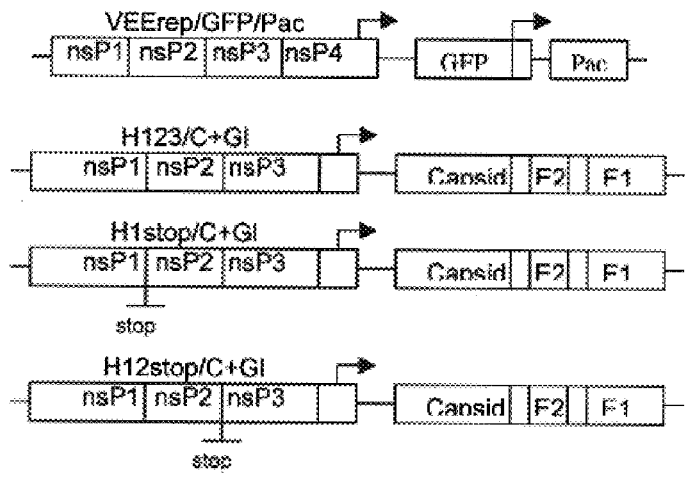
Fig. 12A
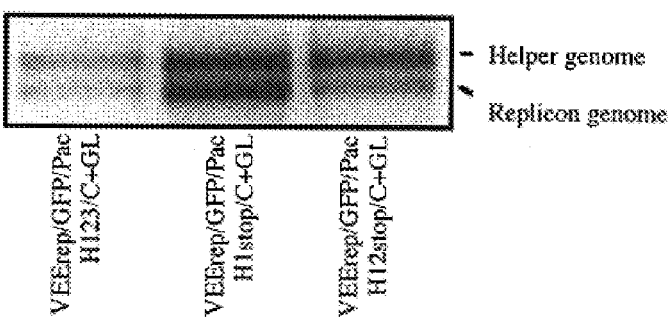
Fig. 12B
| | Titers of packaged VEErep/GFP/Pac replicon (inf.u/ml) | | |
|---|---|---|---|
| | H123/C+Gl MOI 10 inf.u/cell | H1stop/C+Gl MOI 10 inf.u/cell | H12stop/C+Gl MOI 10 inf.u/cell |
| EP | 1-2.5x10$^9$ | 3.75-6.25x10$^6$ | 3.75-7.5e10$^8$ |
| P1 | 1.25-2x10$^9$ | 2.5-6.25x10$^6$ | 0.5-3.75x10$^7$ |
| P2 | 1-2x10$^9$ | NA | NA |
Fig. 12C

Fig. 14E

VENEZUELAN EQUINE ENCEPHALITIS VIRUS REPLICONS WITH ADAPTIVE MUTATIONS IN THE GENOME AND USES THEREOF

CROSS-REFERENCE TO RELATED APPLICATION

This non-provisional applications claims priority to provisional U.S. Ser. No. 60/609,800, filed Sep. 14, 2004, now abandoned.

FEDERAL FUNDING LEGEND

This invention was produced in part using funds obtained through a National Institutes of Health grants AI053135 and AI50537. Consequently, the federal government has certain rights in this invention.

BACKGROUND OF THE INVENTION

1. Field of the Invention

The present invention relates generally to the field of recombinant DNA technology. More specifically, the present invention provides recombinant vectors comprising Venezuelan equine encephalitis virus replicons useful for directing the expression of heterologous gene products.

2. Description of the Related Art

Alphaviruses comprise a set of genetically, structurally, and serologically related arthropod-borne viruses of the Togaviridae family. Alphaviruses are a group of widely distributed human and animal pathogens that include almost 30 currently known members (1-3). Alphavirus genome is single-stranded RNA of positive polarity of almost 12-kb in length with the 5' two thirds of the genome encoding a number of nonstructural proteins (nsP1-4) (4). These proteins are translated directly from the RNA and together with cellular proteins form the RNA-dependent RNA polymerase essential for viral genome replication and transcription of subgenomic RNA. The subgenomic RNA serves as a template for translation of all the structural proteins required for forming viral particles.

Alphavirus replicons are self-replicating RNAs that are useful for directing the expression of heterologous gene products. Replicons mimic the structure of cellular mRNAs in that they contain cap structure at the 5' end and poly(A)-tail at the 3' end. Upon delivery into cells, they are utilized by cellular translational machinery as usual cellular mRNAs, and viral nonstructural proteins are translated to form replicative complexes. Next, replicon RNAs are used as templates for the synthesis of full-length, minus-strand intermediates. These minus-strand intermediates serve as templates for production of large quantities of positive-strand genomic and subgenomic RNAs. Within a few hours post infection, the replicative complexes perform $\sim 10^{4-5}$-fold amplification of the replicon genome that was initially transfected or infected into the cell. The subgenomic RNAs, coding the heterologous sequences, are normally produced in a 10-fold excess to genome RNAs, and become the main mRNAs translated in the infected cells a few hours after beginning of RNA replication. The infection does not spread to other cells because alphavirus structural proteins required for infectious particles formation are not expressed in the replicon-transfected or -infected cells. This has made alphavirus-based replicons such as those derived from Sindbis virus, Semliki Forest virus and Venezuelan equine encephalitis virus very attractive for large-scale production of heterologous proteins.

A main disadvantage of the previous generation of alphavirus replicons is their cytotoxicity and/or sensitivity to IFN. The major known phenomena during replication of alphaviruses and alphavirus-based replicons are transcriptional and translational shut-offs in the infected or transfected cells. Inhibition of both transcription and translation of cellular mRNAs is aimed at suppressing activation of cellular reaction developed in response to replication of virus-specific RNAs. These events downregulate expression and release of cytokines that induce in uninfected cells an antiviral state that makes these cells not susceptible to the next rounds of viral infection. Inhibition of transcription and translation of cellular genes are the critical components of alphavirus-specific cytopathic effect. Development of cytopathic effect is one of the disadvantages of the previously designed Sindbis virus-, Venezuelan equine encephalitis virus- and Semliki Forest virus-based vectors, and long-term expression could not be achieved.

The problem of cytotoxicity was partially resolved by selecting Sindbis virus-based replicons with adaptive mutations in one of the nonstructural proteins nsP2 in U.S. Pat. Nos. 6,458,560 and 6,465,634. The point mutations made the Sindbis virus replicons capable of persisting in cells of vertebrate origin for an indefinite number of passages, and these replicons could express heterologous proteins of interest in addition to dominant selectable markers.

However, the number of cell lines in which the adapted Sindbis replicons could persist is very limited. Only cells with defects in interferon production and/or interferon signaling pathways (BHK-21, Vero and CHO cells) are capable of supporting persistent replication. All other cell lines respond to replication of virus-specific RNAs by IFN-α/β secretion, which, in turn, causes a shutoff of RNA replication in the replicon-containing cells.

Thus, the prior art is still deficient in the lack of improved alphavirus replicon-based vectors with lowered cytotoxicity and/or sensitivity to IFN-α/β. Specifically, the prior art is deficient in the lack of noncytopathic Venezuelan equine encephalitis virus replicon-based vectors useful for developing cell lines for antiviral drug selection or for expression of heterologous proteins. The present invention fulfills this long-standing need and desire in the art.

SUMMARY OF THE INVENTION

The present invention is directed to a Venezuelan equine encephalitis virus replicon RNA. The replicon RNA comprises a sequence encoding nonstructural Venezuelan equine encephalitis virus proteins and one or more heterologous proteins where the third nucleotide in the 5' UTR of the replicon is a guanine. The replicon exhibits reduced cytopathic effect upon cellular infection. RNA in this replicon comprises, in 5' to 3' order (i) a 5' sequence required for nonstructural protein-mediated amplification, (ii) a nucleotide sequence encoding Venezuelan equine encephalitis virus nonstructural proteins nsP1, nsP2, nsP3, and nsP4, (iii) one or more promoters each of which is operably linked to a heterologous nucleic acid sequence, wherein the heterologous nucleic acid sequence replaces one or all of the Venezuelan equine encephalitis virus structural protein genes, (iv) a 3' sequence required for nonstructural protein-mediated amplification, and (v) a polyadenylate tract.

The present invention is also directed to a cDNA copy of the replicon described herein. The cDNA has a 5' promoter that directs synthesis of alphavirus RNA in vivo from cDNA.

The present invention is directed further to an alphavirus particle comprising the replicon described herein.

The present invention is directed further yet to a cell comprising the replicon described herein.

The present invention is directed further still to a method of expressing one or more heterologous proteins in a cell. The method comprises introducing into a cell the replicon described herein and expressing in the cell the heterologous protein encoded by said replicon.

The present invention is directed further still to a method of screening for an inhibitory compound of Venezuelan equine encephalitis virus replication. The method comprises introducing the replicon described herein into a cell and measuring the level of replication of the replicon in the presence or absence of the inhibitory compound. A decreased level of production of heterologous marker protein encoded by the replicon correlates with a lower level of replicon replication in the presence of the inhibitory compound. The lower level of replicon replication in the presence of the inhibitory compound indicates that the inhibitory compound would inhibit replication of Venezuelan equine encephalitis virus.

The present invention is directed further still to a method of screening for an inhibitory compound of eastern equine encephalitis virus replication. The method comprises introducing replicons of eastern equine encephalitis virus into a cell and measuring the level of replication of the replicons in the presence or absence of the inhibitory compound, wherein a decreased level of production of heterologous marker protein encoded by the replicons correlates with a lower level of replicon replication in the presence of the inhibitory compound. The lower level of replication indicates that the inhibitory compound would inhibit replication of eastern equine encephalitis virus.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized. The above may be better understood by reference to certain embodiments thereof which are illustrated in the appended drawings. These drawings form a part of the specification. It is to be noted; however, that the appended drawings illustrate preferred embodiments of the invention and therefore are not to be considered limiting in their scope.

FIGS. 2A-2B depict an analysis of RNA replication and transcription of the subgenomic RNA in the cells transfected with different replicons. In FIG. 2A BHK-21 cells were transfected with 4 μg of the in vitro-synthesized replicons' RNA and equal numbers of electroporated cells ~$10^6$ cells) in six-well Costar plates were labeled with [3H'uridine (20 μCi/ml) in the presence of dactinomycin (1 μg/ml) between 4 and 8 h posttransfection. RNAs were isolated and analyzed by agarose gel electrophoresis as described herein. Lanes contain RNAs from $3 \times 10^5$ cells. The gel was fluorographed and exposed for 60 h. Levels of replicon genome RNA accumulation relative to that of the SINrep/Pac replicon and molar ratio of the subgenome-to-genome RNA synthesis were determined by excision of radiolabeled bands and liquid scintillation counting. N.D. indicates that RNA replication was below the detection limit of the procedure applied. In FIG. 2B RNA replication in the cells containing persisting replicons. After 6 days of selection with puromycin, $10^6$ Pur$^r$ BHK-21 cells containing different replicons were labeled with [$^3$H]uridine (20 μCi/ml) in the presence of dactinomycin (1 μg/ml) for 8 h. RNAs were isolated and analyzed by agarose gel electrophoresis. Lanes contain RNAs from $3 \times 10^5$ cells. The gel was fluorographed and exposed for 6 hays. G and SG indicate positions of replicons' genomic and subgenomic RNAs, respectively.

In FIG. 3A both genomes encoded the same nonstructural proteins derived from Venezuelan equine encephalitis virus TC-83. 5'VEE/SIN had a 5' UTR derived from the Venezuelan equine encephalitis virus TRD strain. Solid boxes and open boxes indicate Venezuelan equine encephalitis virus genome- and SIN genome-derived sequences. In FIG. 3B BHK-21 cells in six-well Costar plates ($5 \times 10^5$ cells/well) were infected with the indicated viruses at an MOI of 1 PFU/cell.

In FIG. 4A the designed replicons encoded the nonstructural proteins and homologous cis-acting elements, i.e., 5'UTR, 3'UTR, subgenomic promoters, and 5'UTRs in the subgenomic RNAs, derived from Venezuelan equine encephalitis virus, EEE and SIN viruses. All of the constructs had one subgenomic promter driving the expression of the Pac gene and a second promoter driving the expression of either GFP or SEAP. Mutations in the 5'UTR of the Venezuelan equine encephalitis virus TC-38-based replicons and in the nsP2 gene of the SIN-based replicon are indicated. In FIG. 4B analysis of alkaline phosphatase expression in the cells carrying persistently replicating Venezuelan equine encephalitis virus and EEE replicons. $2 \times 10^5$ replicon-containing cells were seeded into six-well Costar plates. After 4 h of incubation at 37° C., cells were washed with phosphate-buffered saline and further incubated in 2 ml of complete growth medium. At the indicated time points, 200 μl aliquots of medium were taken and the same volume was added to the wells. Alkaline phosphatase activity was analyzed as described herein. In FIG. 4C analysis of GFP expression in the cells carrying persistently replicating Venezuelan equine encephalitis virus, EEE and SIN replicons with adaptive mutation in nsP2. Cells were analyzed without fixation by flow cytometry on a FACS Vantage (Becton Dickinson).

Figures 6A, 6B:
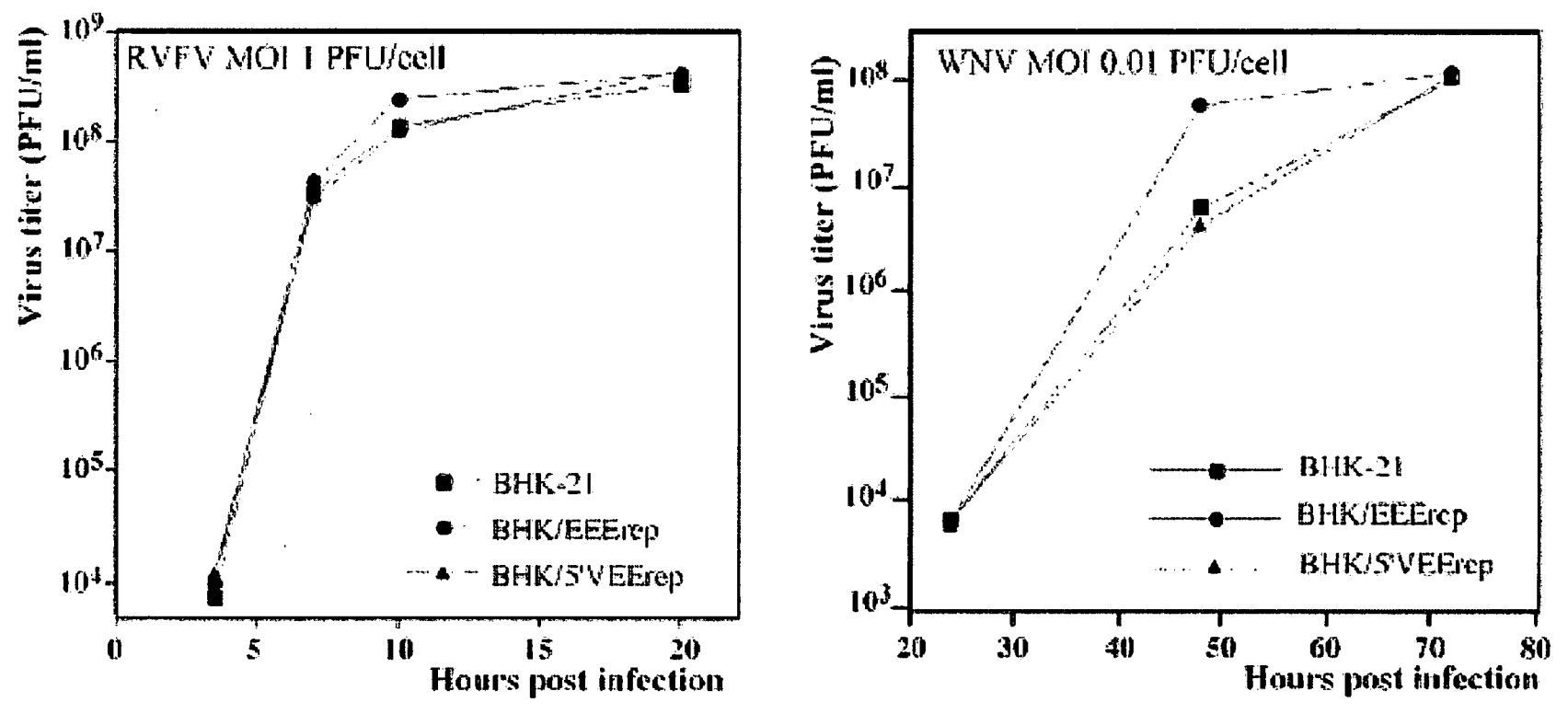
Figures 6C, 6D:
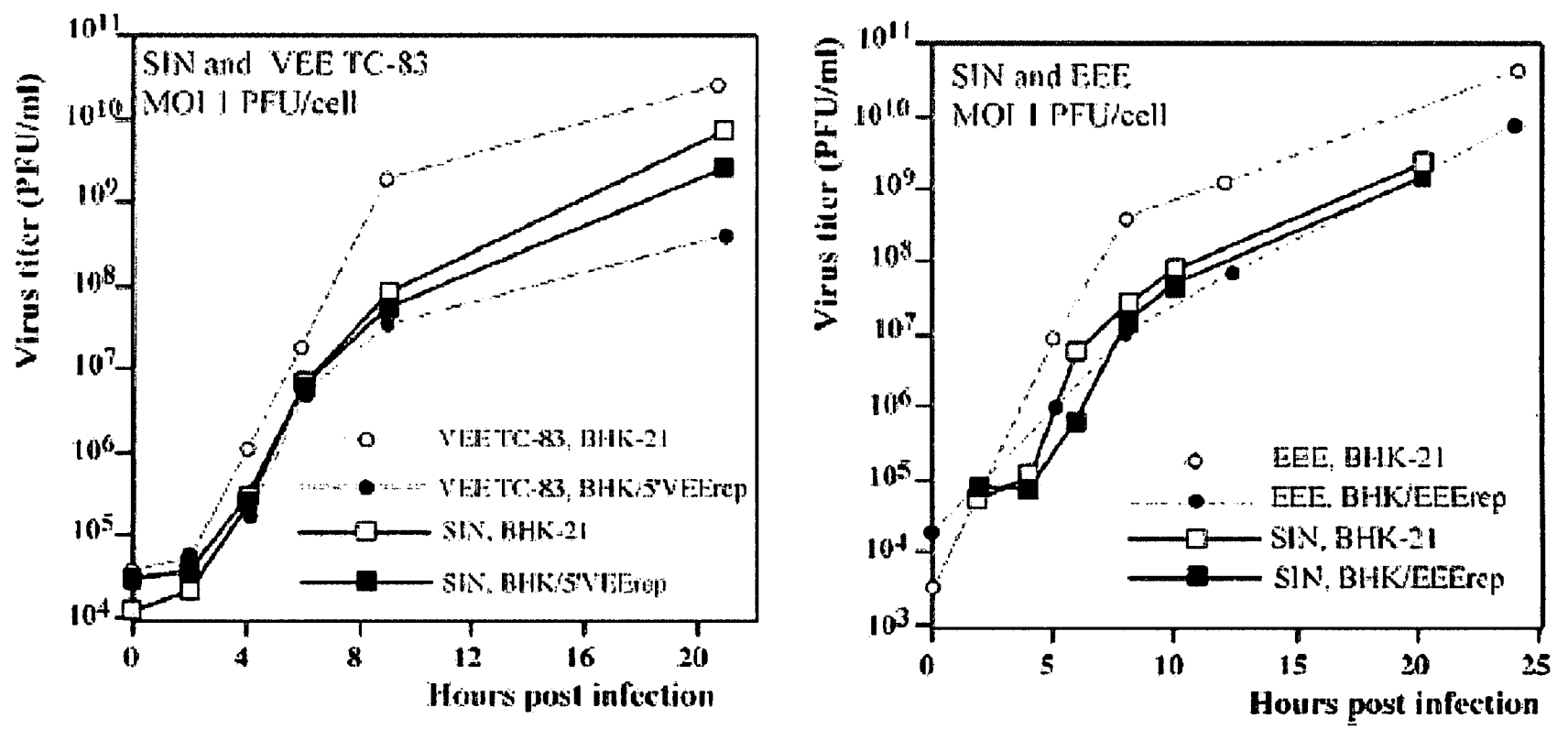

FIGS. 6A-6D depict the analysis of replicons' interference with different viral infections. Cells carrying persistently replicating EEErep/Pac or 5'VEErep/Pac replicons were infected with RVFV MP12 (FIG. 6A), WNV (FIG. 6B), Venezuelan equine encephalitis virus TC-83 and SIN Toto1101 (FIG. 6C), and EEE NA Florida 91 and SIN Toto1101 (FIG. 6D). BHK-21 or Pur$^r$ cells ($5 \times 10^5$) carrying the indicated replicons in six-well Costar plates were infected with viruses at the MOIs indicated. At the indicated times, media were replaced and virus titers were derermined as described herein.

FIGS. 7A-7B show the sequence alignment and adaptive mutations detected in the nsP2 (FIG. 7A) and nsP3 (FIG. 7B) coding sequences of Venezuelan equine encephalitis virus replicons and the mutations found in other alphaviruses and replicons that affect their ability to cause CPE, Venezuelan equine encephalitis, easern equine encephalitis virus (EEE) (5), Sindbis virus (SIN) and Semliki Forest virus (SFV) (6). Residues identical to those in the Venezuelan equine encephalitis virus sequence are indicated by dashes. All of the mutations are highlighted. The mutated amino acids in viral proteins are underlined and in bold. Corresponding amino acids in the proteins of other alphaviruses are indicated by shaded boxes.

In FIG. 8A Huh-7 cells were transfected with 12 μg of 5'VEErep/S/Pac RNA followed by puromycin selection. Colonies of Purr cells were stained after 20 days of drug treatment. In FIG. 8B Huh-7 cells were transfected with 12 μg of 5'VEErep/S/Pac RNA containing the $P_{773} \rightarrow S$ mutation in nsP2 and treated with puromycin for 10 days. No cell death was detected to CPE caused by replication of virus-specific RNAs or drug treatment. In FIG. 8C different Purr, "GFP-expressing cell lines were generated by transfection of 4 μg of 5'VEErep/S/GFP/Pac RNA followed by puromycin selection. In FIG. 8D BHK-21 cells were transfected with 4 μg of in vitro-synthesized prplicons' RNA and equal number of electroporated cells, $\sim 10^6$ cells, in six-well Costar plates were labeled with [$^3$H]uridine (30 μCi/ml) in the presence of dactinomycin (1 μg/ml) at 3 to 7 h posttransfection. RNAs were isolated and analyzed by agarose gel electrophoresis as described herein. Lanes contain RNAs from $25 \times 10^5$ cells. G and SG indicate positions of replicons' genomic and subgenomic RNAs.

FIGS. 9A-9C depict packaging of Venezuelan equine encephalitis virus and SIN replicons in BHK-21 cells using helpers with deletions of nsP1-4-coding genes. FIG. 9A is a schematic representation of SIN and VEE replicons and helper genomes. All of the Venezuelan equine encephalitis virus helpers, Hvee/C+GI, Hvee/C and Hvee/GI, had natural 5'UTR, derived from Venezuelan equine encephalitis virus TC-83 virus genome and deletion of nt 520-7290. Hsin/C+GI and tRNA/Hsin/C+GI had natural SIN 5'UTR and the 5' tRNA$^{Asp}$ sequence derived from the naturally occurring SIN DI RNA, respectively. SIN helpers contained a deletion of nt 421-7334 of SIN genome. FIG. 9B shows titers of packaged Venezuelan equine encephalitis virus and SIN replicons after electroporation and further passaging of the samples. BHK-21 cells were co-transfected with VEErep/GFP/Pac and SIN-rep/GFP replicons and indicated helper RNAs. Harvested viral particles were used for the next round of infection of naïve BHK-21 cells at the indicated MOIs (measured in inf.u/cell). Viruses were harvested after development of CPE and used for further passaging. Titers refer to unconcentrated virus-containing media. Numbers in the brackets indicate titers in colony-forming units (CFU/ml). All of the experiments were performed multiple times and generated very reproducible titers. NA indicates "not applicable," because concentration of the packaged replicons after passage 1 was insufficient for infecting cells on the next passage at an MOI of 10 inf.u/cell. FIG. 9C depicts packaging of replicon and helper RNAs into viral particles. $^{32}$P-labeled RNAs were isolated from the viral particles released from the cells co-transfected with the indicated replicon and helper RNAs as described herein. RNA isolated from SIN virus was used as a positive control.

FIG. 10 depicts the accumulation of the DI RNAs in the samples of Venezuelan equine encephalitis virus TC-83 passaged in BHK-21 cells at high MOI as described herein. RNA labeling in the presence of ActD and analysis were performed for the samples harvested after passage 1, 4, 6, 8 and 10 as described. Virus-specific RNAs and viral titers are indicated.

FIG. 11A is a schematic representation of Venezuelan equine encephalitis virus replicons and helper genomes. All of the helpers were derived from the Venezuelan equine encephalitis virus TC-83 genome, in which nt 5702-7500 encoding almost the entire nsP4 was deleted. The TGA codon was inserted after nt 5701. Hstop123/C+GI helper contained an additional insertion of 4 nt sequence after nt 1620. In FIG. 11B shows titers of packaged Venezuelan equine encephalitis virus replicons after electroporation and further passaging of the samples. BHK-21 cells were co-transfected with VEErep/GFP/Pac replicon and indicated helper RNAs. Harvested viral particles were used for the next round of infection of naïve BHK-21 cells at the indicated MOIs (measured in inf.u/cell). Viruses were harvested after the development of CPE and used for further passaging. Titers refer to unconcentrated harvested virus-containing media. NA indicates "not applicable," because concentration of the packaged replicons after the previous passage was insufficient for infecting cells at an MOI of 10 inf.u/cell. FIG. 11C shows growth curves of the tri-component genome Venezuelan equine encephalitis virus (VEErep/GFP/Pac+H123/C+H123/GI) and VEE TC-83. BHK-21 cells infected at an MOI of 10 inf.u/cell or PFU/cell with tri-component virus and VEE TC-83, respectively. At the indicated times, media were replaced and titers of packaged replicons and virus were determined as described. FIG. 11D shows packaging of replicon and helper RNAs into viral particles. $^{32}$P-labeled RNAs were isolated from the viral particles released from the cells co-transfected with VEErep/GFP/Pac and indicated helper RNAs. RNA isolated from VEE TC-83 virus was used as a positive control.

FIGS. 12A-12C depict packaging of Venezuelan equine encephalitis virus replicons in BHK-21 cells using helpers with deletions of nsP4-coding gene. FIG. 12A is a schematic representation of Venezuelan equine encephalitis virus replicons and helper genomes. All of the helpers were derived from the Venezuelan equine encephalitis virus TC-83 genome, in which nt 5702-7500 were deleted. In all of them, TGA codons were inserted after the last amino acid of nsP3. The TGA codon was also inserted after the last amino acid of nsP1 and nsP2 in H1stop/C+GI and H12stop/C+GI, respectively. FIG. 4B shows packaging of replicon and helper RNAs into viral particles. $^{32}$P-labeled RNAs were isolated from the viral particles released from the cells co-transfected with the indicated replicon and helper RNAs as described. FIG. 12C shows titers of packaged Venezuelan equine encephalitis virus replicons after electroporation and further passaging of the samples. BHK-21 cells were co-transfected with VEErep/GFP/Pac replicon and indicated helper RNAs. Harvested viral particles were used for the next round of infection of naïve BHK-21 cells at the indicated MOIs measured in inf.u/cell. Viruses were harvested after development of CPE. Titers refer to unconcentrated harvested media. NA indicates "not applicable," because concentration of the packaged replicons after the previous passage was insufficient for infecting cells at an MOI of 10 inf.u/cell.

FIG. 13A is a schematic representation of SIN replicons and helper genomes. FIG. 13B shows packaging of replicon and helper RNAs into viral particles. $^{32}$P-labeled RNAs were isolated from the viral particles released from the cells co-transfected with the indicated replicon and helper RNAs. RNA isolated from SIN virus was used as a positive control. FIG. 13C shows replication of SIN-specific RNAs in BHK-21 cells after electroporation (upper panel) and during passage 1 performed at an MOI 10 inf.u/cell. At 3 h post transfection or post infection, media were replaced by the same media supplemented with dactinomycin (1 μg/ml) and [$^3$H]uridine (20 μCi/ml). After 4 h of incubation at 37° C., RNAs were isolated and analyzed as described. SINrep/GFP and Hsin123/C plus Hsin123/GI helpers, lanes 1; SINrep/GFP and Hsin123/C+GI helper, lanes 2; SINrep/GFP and Hsin/C plus Hsin/GI helpers, lanes 3; SINrep/GFP and Hsin/C+GI helper, lanes 4; SINrep/GFP and tRNA/Hsin/C+GI helper, lanes 5. FIG. 13D shows titers of packaged Venezuelan equine encephalitis virus replicons after electroporation and further passaging of the samples. BHK-21 cells were co-transfected with SINrep/GFP replicon and indicated helper RNAs. Harvested viral particles were used for the next round of infection of naïve BHK-21 cells at the indicated MOIs. Viruses were harvested after development of CPE. Titers refer to unconcentrated harvested media. NA indicates "not applicable," because concentration of the packaged replicons after the previous passage was insufficient for infecting cells at an MOI of 10 inf.u/cell.

FIGS. 14A-14E depict virus replication and synthesis of virus-specific RNAs in SIN Toto1101- and VEE TC-83-infected cells. In FIGS. 14A-14B BHK-21 cells (5×10$^5$ cells in 35-mm dishes) were infected with SIN Toto1101 or VEE TC-83 at an MOI of 10 PFU/cell. At the indicated times, proteins were pulse-labeled with [$^{35}$S]methionine as described herein and analyzed on sodium dodecyl sulfate-10% polyacrylamide gels. The gels were dried and autoradiographed (FIG. 14A) or analyzed on a Storm 860 PhoshorImager (FIG. 14B). The levels of synthesis of virus-specific proteins were determined by measuring radioactivity in the protein band corresponding to capsid and were normalized to the number of cysteins and methionines in these proteins. In FIGS. 14C-14D BHK-21 cells (5×10$^5$ cells in 35-mm dishes) were infected with SIN Toto1101 or VEE TC-83 at an MOI of 10 PFU/cell. At the indicated times, media were replaced by the same media supplemented with dactinomycin (1 μg/ml) and [$^3$H]uridine (20 μCi/ml). After 4 h of incubation at 37° C., RNAs were isolated and analyzed as described (FIG. 14C). The levels of viral genome replication were determined by excising the bands corresponding to 49S viral genome RNA from the gel shown on FIG. 14C, followed by measuring radioactivity by scintillation counting (FIG. 14D). In FIG. 14E BHK-21 cells (5×10$^5$ cells in 35-mm dishes) were infected with SIN Toto1101 or Venezuelan equine encephalitis virus TC-83 at an MOI of 10 PFU/cell. At the indicated times, the media were replaced and virus titers were determined as described.

DETAILED DESCRIPTION OF THE INVENTION

Figure 1:
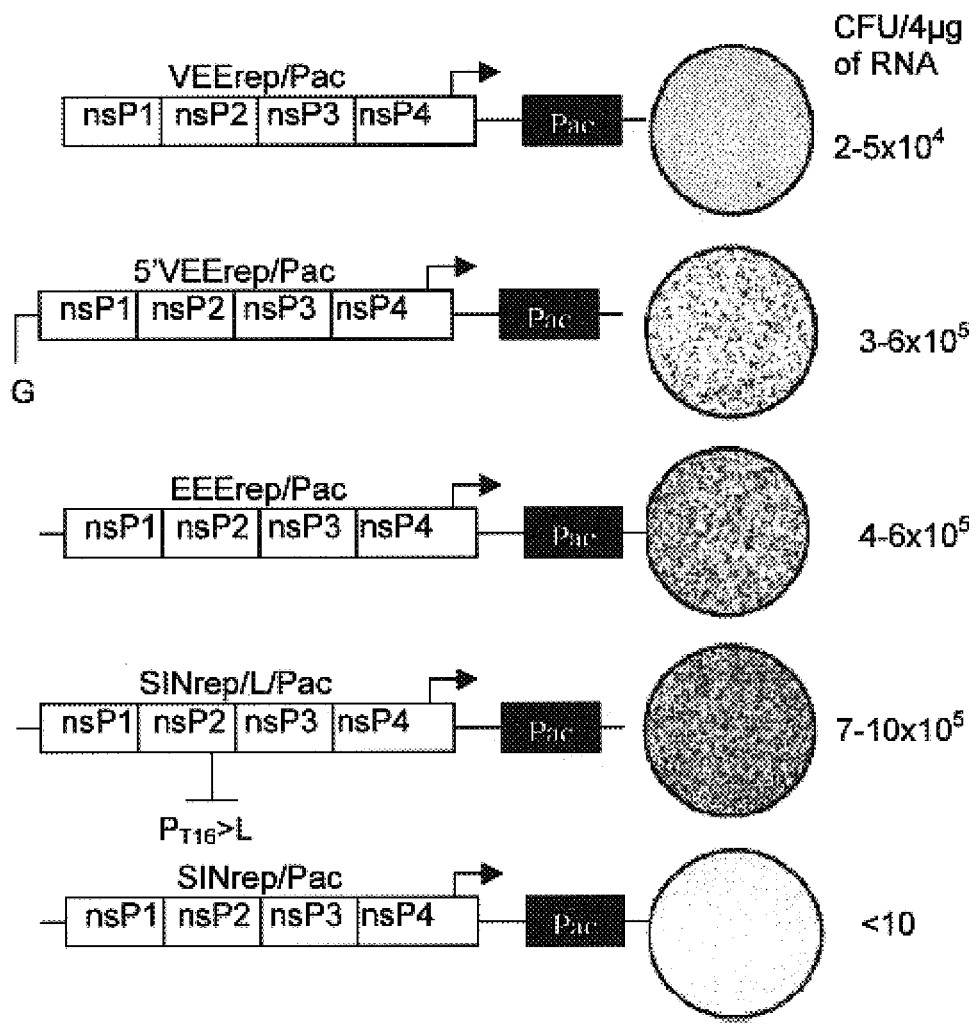
FIG. 1 is a schematic representation of replicons and their ability to persistently replicate in BHK-21 cells. The positions of the mutations in the Venezuelan equine encephalitis virus 5' UTR and SIN nsP2 coding gene are indicated. BHK-21 cells were transfected by 4 μg of each in vitro-synthesized replicon RNA using electroporation and different dilutions of the cells were seeded into 100-mm dishes. Puromycin selection (10 μg/ml) was applied 24 h postransfection. After 5 days of incubation under puromycin, dishes containing 1% of electroporated cells were stained with crystal violet. The efficiency of focus formation was calculated based on the number of foci in the dishes containing fewer electroporated cells.

In one embodiment of the present invention there is provided Venezuelan equine encephalitis virus replicon RNA comprising a sequence encoding nonstructural Venezuelan equine encephalitis virus proteins and one or more heterologous proteins, wherein the third nucleotide in the 5' UTR of the replicon is a guanine and the replicon exhibits reduced cytopathic effect upon cellular infection.

In this embodiment one of the heterologous proteins may be a selection marker. Examples of a selection marker are a fluorescent protein, puromycin acetyltransferase, or neomycin acetyltransferase. Also, in this embodiment the RNA may comprise, in 5' to 3' order (i) a 5' sequence required for nonstructural protein-mediated amplification, (ii) a nucleotide sequence encoding Venezuelan equine encephalitis virus nonstructural proteins nsP1, nsP2, nsP3, and nsP4, (iii) one or more promoters each of which is operably linked to a heterologous nucleic acid sequence, wherein the heterologous nucleic acid sequence replaces one or all of the Venezuelan equine encephalitis virus structural protein genes, (iv) a 3' sequence required for nonstructural protein-mediated amplification, and (v) a polyadenylate tract. In one aspect RNA may encode one or more of a mutated nonstructural protein nsP2 having a Leu at amino acid position 739, nsP2 having a Ser at amino acid position 773, or nsP3 having a Pro at amino acid position 121. In this aspect the encoded nonstructural proteins may be one or more of a mutated nonstructural protein nsP2 having a Leu residue at amino acid position 739, nsP2 having a Ser residue at amino acid position 773, or nsP3 having a Pro residue at amino acid position 121.

In a related embodiment there is provided a cDNA copy of the replicon RNA described supra wherein the cDNA has a 5' promoter that directs synthesis of alphavirus RNA in vivo from cDNA. An example of a 5' promoter is a eukaryotic RNA polymerase II promoter.

In another embodiment of the present invention there is provided an alphavirus particle comprising the replicon RNA described supra. Related to this embodiment there is provided a cell comprising the replicon RNA described supra. Examples of cells are a mammalian cell, an insect cell, or an avian cell. Further to this embodiment the cell secretes or responds to interferon.

In yet another embodiment of the present invention there is provided a method of expressing one or more heterologous proteins in a cell, comprising introducing the replicon RNA described supra into a cell; and expressing the heterologous protein encoded by the replicon in the cell. In this embodiment the replicon RNA may be introduced into the cell by infection or transfection. Also in this embodiment the cell may secrete or respond to interferon.

In still another embodiment of the present invention provides a method of screening for an inhibitory compound of Venezuelan equine encephalitis virus replication, comprising introducing the replicon RNA described supra into a cell; and measuring the level of replication of the replicon RNA in the presence or absence of the inhibitory compound, wherein a decreased level of production of heterologous marker protein encoded by the replicon correlates with a lower level of replicon replication in the presence of the inhibitory compound; where the lower level of replicon replication in the presence of the inhibitory compound indicating that the inhibitory compound would inhibit replication of Venezuelan equine encephalitis virus. In this embodiment the replicon RNA, introducing the replicon RNA into the cell and cell is as described supra.

In a related embodiment there is provided a method of screening for an inhibitory compound of eastern equine encephalitis virus replication, comprising introducing into a cell replicons of eastern equine encephalitis virus; and measuring the level of replication of the replicons in the presence or absence of the inhibitory compound, wherein a decreased level of production of heterologous marker protein encoded by the replicons correlates with a lower level of replicon replication in the presence of the inhibitory compound, where the lower level of replication indicates that the inhibitory compound would inhibit replication of eastern equine encephalitis virus. In this embodiment the replicon RNA, introducing the replicon RNA into the cell and cell is as described supra.

As used herein, the terms "replicon RNA" refers to RNA which contains all of the genetic information required for directing its own amplification or self-replication within a permissive cell. To direct its own replication, the RNA molecule 1) encodes polymerase, replicase, or other proteins which may interact with viral or host cell-derived proteins, nucleic acids or ribonucleoproteins to catalyze the RNA amplification process; and 2) contain cis-acting RNA sequences required for replication and transcription of the subgenomic replicon-encoded RNA. These sequences may be bound during the process of replication to its self-encoded proteins, or non-self-encoded cell-derived proteins, nucleic acids or ribonucleoproteins, or complexes between any of these components. An alphavirus-derived replicon RNA molecule should contain the following ordered elements: 5' viral or defective-interfering RNA sequence(s) required in cis for replication, sequences coding for biologically active alphavirus nonstructural proteins (e.g., nsP1, nsP2, nsP3, and nsP4), promoter for the subgenomic RNA, 3' viral sequences required in cis for replication, and a polyadenylate tract. Generally, the term replicon RNA refers to a molecule of positive polarity, or "message" sense, and the replicon RNA may be of length different from that of any known, naturally-occurring alphavirus. In preferred embodiments, the replicon RNA does not contain the sequences of at least one of structural viral protein; sequences encoding structural genes are usually substituted with heterologous sequences. In those instances where the replicon RNA is to be packaged into a recombinant alphavirus particle, it must contain one or more sequences, so-called packaging signals, which serve to initiate interactions with alphavirus structural proteins that lead to particle formation.

As used herein, "subgenomic RNA" refers to a RNA molecule of a length or size which is smaller than the genomic RNA from which it was derived. The subgenomic RNA should be transcribed from an internal promoter, whose sequences reside within the genomic RNA or its complement. Transcription of the subgenomic RNA may be mediated by viral-encoded polymerase(s) associated with host cell-encoded proteins, ribonucleoprotein(s), or a combination thereof. In preferred embodiments, the subgenomic RNA is produced from a replicon according to the invention and encodes or expresses a gene(s) or sequence(s) of interest. Instead of the subgenomic promoter, the subgenomic RNA can be placed under control of internal ribosome entry site (IRES) derived from EMC, BVD, polio-, FMD or hepatitis C viruses.

Thus, the present invention provides replicons based on the genome of the Venezuelan equine encephalitis (VEE) virus vaccine strain TC-83, which are detectably less cytopathic than replicons based on previous wild type epizootic strain Trinidad Donkey genome. In addition, a critical mutation was introduced into the 5' untranslated region (5' UTR) of the TC-83 genome during the development of 5'VEErep/Pac replicon ($A_3 \rightarrow G$). Replacement of nucleotide $A_3$ by G was previously found not only to increase the resistance of Venezuelan equine encephalitis virus to IFN-$\alpha/\beta$. It also decreased translation of nonstructural proteins and strongly reduced cytopathicity of the new construct.

The Venezuelan equine encephalitis virus replicon RNA comprises a sequence encoding one or more heterlogous proteins. For example, a heterologous protein may be, but not limited to, a selection marker. Representative selection markers are a fluorescent protein, puromycin acetyltransferase or neomycin acetyltransferase.

Preferably, the replicon RNA may comprise in 5' to 3' order (i) a 5' sequence required for nonstructural protein-mediated amplification, (ii) a nucleotide sequence encoding Venezuelan equine encephalitis virus nonstructural proteins nsP1, nsP2, nsP3, and nsP4, (iii) one or more promoters each of which is operably linked to a heterologous nucleic acid sequence such that the heterologous nucleic acid sequence replaces one or all of the Venezuelan equine encephalitis virus structural protein genes, (iv) a 3' sequence required for nonstructural protein-mediated amplification, and (v) a polyadenylate tract. More preferably, the nonstructural proteins encoded by the RNA may be one or more of one or more of a mutated nonstructural protein nsP2 having a Leu residue at amino acid position 739, nsP2 having a Ser residue at amino acid position 773, or nsP3 having a Pro residue at amino acid position 121.

Replicons of Venezuelan equine encephalitis virus can be easily manipulated in vitro by standard genetic engineering procedures. Any heterologous gene containing no introns can be cloned into replicons within a few days for their further expression in eucaryotic cells. Replicon RNAs can be efficiently synthesized in vitro using T7 or SP6 polymerases, because the replicon-encoding plasmids contain specific promoters cloned upstream of the virus-specific 5' end. These RNAs are usually delivered or transferred into cells by standard liposome- or electroporation-mediated techniques.

Thus, the present invention also provides an alphavirus particle comprising the Venezuelan equine encephalitis virus replicon RNAs described herein. In addition, the present invention also provided a cell comprising these Venezuelan equine encephalitis virus replicon RNAs. Preferred cells are a mammalian cell, an insect cell, or an avian cell. It is contemplated that these cells either secrete interon or respond to interferon.

Alternatively, cDNA copies of the replicons can be cloned into plasmids under the control of eucaryotic RNA polymerase II-dependent promoters (CMS, RSV or other promoters) and transfected into cells in plasmid DNA form. In this latter case, first copies of the replicons' RNAs are transcribed by cellular RNA polymerase II, are transported to the cytoplasm, and then begin self-replication. In addition, by using so-called helpers, replicon RNAs can be packaged into infectious alphavirus particles and delivered into cells by infection. Thus, the present invention provides a cDNA copy of the replicon RNA described herein that has a 5' promoter that directs synthesis of alphavirus RNA in vivo from cDNA. Preferably, the 5' promoter is a 5' promoter is a eukaryotic RNA polymerase II promoter.

The present Venezuelan equine encephalitis (VEE) virus TC-83-based replicons comprising 5' UTR derived from the Venezuelan equine encephalitis TRD genome and adaptive mutations in the nonstructural genes have a number of critical features that make their application more advantageous than that of previously designed constructs. These replicons are noncytopathic, strongly resistant to IFN-α/β and can be used for expression of heterologous genes in a wide variety of cell lines. The expression of heterologous proteins is very stable for more than 10 passages. Persistent replicons do not interfere with other viral infections and can be used for trans-complementation of genetic defects in other viruses during their propagation in tissue culture.

The Venezuelan equine encephalitis virus replicon RNAs are useful in screening for inhibitory compounds for Venezuelan equine encephalitis replication. After introducing a Venezuelan equine encephalitis virus replicon into a cell, the level of replicon replication in the presence and absence of the inhibitory compound correlates with the level of production of a heterologous marker protein comprising the RNA. A lower level of replicon replication in the presence of the inhibitory compound is indicative that the inhibitory compound would inhibit replication of Venezuelan equine encephalitis virus. The replicon is introduced into the cell via any effective standard method described. Preferably, the cell into which the replicon is introduced is capable of secreting or responding to interferon. Effective assays to determine replicon replication and heterologous marker protein production are known and standard in the art.

Also, it is contemplated that this screening method is useful for identifying inhibitory compounds of eastern equine encephalitis (EEE) virus replication. Replicons for EEE having a sequence encoding a heterologous marker as described are introduced into appropriate cells. Levels of EEE replicon replication and heterologous marker protein production in the presence or absence of the potential inhibitory compound are monitored and measured as for VEE replicons.

The following examples are given for the purpose of illustrating various embodiments of the invention and are not meant to limit the present invention in any fashion.

EXAMPLE 1

Materials and Methods
Cell Cultures
BHK-21 cells were provided by Paul Olivo (Washington University, St. Louis, Mo.). They were maintained at 37° C. in alpha minimum essential medium (αMEM) supplemented with 10% fetal bovine serum (FBS) and vitamins.

Plasmid Constructs
The high-copy-number plasmid encoding the EEE nonstructural proteins from the genome of North American strain Florida 91 was provided by Michael Parker (U.S. Army Medical Research Institute for Infectious Diseases). The high-copy-number plasmid carrying the VEE TC-83 strain genome was described elsewhere (5). TC-83 is a live attenuated vaccine strain of VEE that is available for vaccination of laboratory workers and military personnel. It was developed by serial passaging of the virulent, subtype IAB Trinidad donkey (TRD) Venezuelan equine encephalitis virus strain in cell culture (7). SINrep/L/Pac and SINrep/Pac replicon-encoding plasmids were described elsewhere (8). They were previously referred to as pSINrep19/Pac and pTSG/Pac, respectively. The names were changed to make them consistent with other names of the constructs developed in this work.

Standard recombinant DNA techniques were used for all plasmid constructions. All of the required sequence modifications were carried out using PCR-based mutagenesis and sequences were verified by sequencing of the cloned fragments. The genetic material from the Venezuelan equine encephalitis virus TC-83 strain and the EEE North American strain Florida 91 was cloned into a pToto1101 plasmid (9) to replace the entire SIN genome.

The construct, pEEErep/Pac, contained the promoter for SP6 RNA polymerase, followed by nucleotides (nt) 1 to 7594 of the EEE genome, a synthetic TCTAGAGCTTACC sequence (SEQ ID NO: 1) that came with a puromycin acetyltransferase (Pac)-encoding cassette, a 764-nt-long sequence containing the entire gene of the selectable marker Pac and a 356-nt-long sequence of the EEE 3' UTR followed by poly(A) and a NotI restriction site. pVEErep/Pac contained the promoter for SP6 RNA polymerase, followed by nt 1 to 7561 of the VEE TC-83 genome, a synthetic TCTAGAGCTTACC sequence (SEQ ID NO: 1), a 676-nt-long sequence encoding the entire Pac gene and a 330-nt-long sequence of VEE TC-83 that included the 3' end of the E1-encoding gene and the 3' UTR followed by poly(A) and an MluI restriction site. p5'VEErep/Pac carried essentially the same replicon with a single substitution: the A in the third position of the 5' UTR was replaced by G.

pEEErep/SEAP/Pac also contained an SP6 promoter, followed by nt 1 to 7594 of the EEE genome, a synthetic TCTAGGTGAGC sequence (SEQ ID NO: 2) that came with a secreted alkaline phosphatase (SEAP)-encoding cassette, a 1597-nt-long sequence carrying the entire sequence of the SEAP gene derived from pSEAP2-Basic (Clontech), nt 7183 to 7594 of the EEE genome that encoded the subgenomic promoter, a synthetic TCTAGAGCTTACC sequence (SEQ ID NO: 1), a 764-nt-long Pac gene and a 356-nt-long sequence of the EEE 3' UTR followed by poly(A) and a NotI restriction site.

pEEErep/GFP/Pac had a structure similar to that of pEEErep/SEAP/Pac, but the SEAP gene was replaced by a green fluorescent protein (GFP) coding sequence. p5'VEErep/SEAP/Pac contained the promoter for SP6 RNA polymerase, followed by nt 1 to 7561 of the VEE TC-83 genome with A3 in the 5' UTR replaced by G, a synthetic TCTAGGTGAGC sequence (SEQ ID NO: 2), a 1597-nt-long sequence carrying the entire SEAP gene, nt 7501 to 7561 of the VEE genome (carrying the subgenomic promoter), a synthetic TCTAGAGCTTACC sequence (SEQ ID NO: 1), a 676-nt-long sequence carrying the entire Pac gene, and a 330-nt-long sequence of VEE TC-83 that included the 3' end of the E1-encoding gene and the 3' UTR followed by poly(A) and an MluI restriction site. p5'VEErep/GFP/Pac had a similar structure, but the SEAP gene was replaced by a GFP coding sequence. p5'VEE/SIN carried the promoter for SP6 RNA polymerase, followed by nt 1 to 7535 of the VEE TC-83 genome, with A3 in the 5' UTR replaced by G, nt 7601 to 11486 of the SIN genome carrying the SIN structural genes, with T7626 replaced by C to preserve the secondary structure of the 5' UTR in the subgenomic RNA, a 273-nt-long fragment of the VEE TC-83 genome containing the 3' end of the E1 coding sequence, the 3' UTR, poly(A), and an MluI restriction site.

pHsin/C+GI, pHsin/C, pHsin/GI and ptRNA/Hsin/C+GI helper-coding plasmids were previously described (10-11). They were formerly referred to as DH-BB(5'SIN), BB/C, BB/GI and DH-BB, respectively. The terminology was changed to make their names consistent with those of other constructs developed herein.

These helpers encoded SIN genomes with either natural 5'UTR or tRNA$^{Asp}$ 5'UTR, derived from naturally occurring SIN DI RNA. The deletion of nt 421-7334 covered nsP2, nsP3, and most of the nsP1- and nsP4-coding regions. pHsin123/C+GI plasmid encoded SIN genome with deletion of nt 5769-7334. This helper genome was capable of expressing nsP1, nsP2 and nsP3, and its subgenomic RNA encoded all of the SIN structural proteins. pHsin123/GI and pHsin123/C helper-containing plasmids had the same deletion of the nsP4 gene as did pHsin123/C+GI, but the subgenomic RNAs were derived from the previously described pDH-BB/C and pDH-BB/GI (11) and were capable of expressing only SIN capsid and SIN glycoproteins, respectively.

pHvee/C+GI, pHvee/C and pHvee/GI encoded VEE helper RNAs, cloned under control of the SP6 promoter. They contained a deletion of nt 520-7290 covering almost the entire Venezuelan equine encephalitis virus P1234 polyprotein, encoding the RdRp. The Hvee/C+GI helper contained the entire subgenomic RNA encoding all of the Venezuelan equine encephalitis virus TC-83 structural proteins. The subgenomic RNA of Hvee/C encoded only Venezuelan equine encephalitis virus capsid, because nt 8387-11326 were deleted. Hvee/GI helper contained Venezuelan equine encephalitis virus subgenomic RNA, in which nt 7805-7897, the coding cluster of positively charged amino acids, was deleted to make the capsid incapable of RNA-binding.

pH123/C+GI encoded the helper genome containing a deletion of nt 5702-7500, covering almost the entire nsP4-coding sequence, with a TGA codon inserted downstream of the nsP3-coding sequence, at 5701 position. This helper contained the entire subgemomic RNA encoding all of the Venezuelan equine encephalitis virus TC-83 structural proteins. Subgenomic RNA of H123/C helper encoded only the Venezuelan equine encephalitis virus capsid, and nt 8387-11326 was deleted. H123/GI helper contained Venezuelan equine encephalitis virus subgenomic RNA with the deletion of nt 7805-7897, making the capsid incapable of RNA binding.

The Hstop123/C+GI helper construct was essentially the same as H123/C+GI, except for the insertion of a TCGA sequence after nt 1620. These 4 nucleotides were inserted to destroy the open reading frame (ORF). H1stop/C+GI and H12stop/C+GI helpers had the same genome structure as H123/C+GI, except for insertion of TGA codons immediately after the nsP1- and nsP2-coding sequences, respectively. Standard recombinant DNA techniques were used for all plasmid constructions and all of the required sequence modifications were carried out using PCR-based mutagenesis or by using existing, convenient restriction sites.

RNA Transcriptions

Plasmids were purified by centrifugation in CsCl gradients. Before the transcription reaction, the VEE replicon- and VEE helper-coding plasmids were linearized using an MluI restriction site located downstream of the poly(A) sequence. SIN replicon- and SIN helper-containing plasmids were linearized using an XhoI restriction enzyme. RNAs were synthesized by SP6 RNA polymerase in the presence of a cap analog using previously described conditions (10). The yield and integrity of transcripts were analyzed by gel electrophoresis under non-denaturing conditions. Aliquots of transcription reactions were used for electroporation without additional purification.

RNA Transfections

BHK-21 cells were electroporated by previously described conditions (12). 4 µg of in vitro-synthesized replicon RNA was always used and 6 µg of each helper RNA for electroporation. Packaged replicons were harvested 24 to 28 h post electroporation. For measuring the titers of packaged replicons in infectious unit per ml (inf.u/ml), BHK-21 cells were seeded at a concentration of $5\times10^5$ cells/35-mm dish. After 4 h incubation at 37° C., monolayers were infected with 10-fold dilutions of the samples and incubated for 1 h at 37° C. and then 1 ml of complete medium was added to the wells. Incubation continued either at 37° C. for 6-8 h or at 30° C. for 16-18 h. The numbers of GFP-expressing cells were evaluated on an inverted fluorescent microscope. To measure the concentration of the packaged VEE replicon, VEErep/GFP/Pac, in colony-forming units (CFU/ml), cells infected with ten-fold dilutions of the packaged replicons were incubated in complete media, supplemented with 5 µg/ml of puromycin. Colonies of Pur$^R$ cells were stained with crystal violet after 5-7 days of incubation at 37° C.

Infectious Center Assay

In standard experiments, 1 µg of in vitro-synthesized, full-length RNA transcripts of viral genomes was used per electroporation. Tenfold dilutions of electroporated BHK-21 cells were seeded in six-well Costar plates containing sub-confluent naive cells. After 1 h of incubation at 37° C. in a 5% CO$_2$ incubator, cells were overlaid with 2 ml of minimum essential medium containing 0.5% Ultra-Pure agarose supplemented with 3% FBS. Plaques were stained with crystal violet after 2 days' incubation at 37° C.

Viral Replication Analysis

BHK-21 cells were seeded at a concentration of $5\times10^5$ cells/35-mm dish. After 4 h incubation at 37° C., monolayers were infected with MOIs, as indicated in figure legends and overlaid with 1 ml of complete medium. At indicated times post infection, media were replaced and virus titers or titers of packaged replicons in the harvested samples were determined by a plaque assay on BHK-21 cells as previously described (Lemm et al., 1990) and by the above described method, respectively.

Generation of VEE TC-83 DI RNAs $2.5\times10^6$ BHK-21 cells were infected with 1 ml of the VEE vaccine strain TC-83 samples harvested after the previous passage. Viruses were harvested after development of profound cytopathic effect (CPE) that usually occurred within 30 h post infection. Titers were determined by a standard plaque assay on BHK-21 cells (13). Accumulation of the DI RNAs was detected by infecting $5\times10^5$ BHK-21 cells with 200 µl of undiluted virus samples, followed by metabolic RNA labeling in 0.8 ml αMEM supplemented with 10% FBS, 1 µg/ml of ActD and 20 µCi/ml of [$^3$H]uridine at 37° C. between 3 and 7 h post infection. RNAs were isolated from the cells by TRIzol reagent, as recommended by the manufacturer (Invitrogen). They were denatured with glyoxal in dimethyl sulfoxide and analyzed by agarose gel electrophoresis using the previously described conditions (10).

RNA Analysis

Cells were transfected with in vitro-synthesized RNAs or, in some experiments, infected with viral particles and seeded into 35-mm dishes at a concentration of $10^6$ cells/dish. After incubation at 37° C. for 16 h, cells were washed with phosphate-free Dulbecco's Modified Eagle Medium (DMEM) and the incubation continued in 0.8 ml of the same phosphate-free DMEM supplemented with 1% FCS and 50

μCi/ml of [$^{32}$P]phosphoric acid at 37° C. for 8 h. Virus particles were harvested before CPE development and pelleted by centrifugation in the tabletop Optima ultracentrifuge (Beckman) in TLA-55 rotor at 52,000 rpm for 1 h at 4° C. RNAs were isolated from the pelleted viruses by TRIzol reagent, as recommended by the manufacturer (Invitrogen). They were denatured with glyoxal in dimethyl sulfoxide and analyzed by agarose gel electrophoresis using the previously described conditions (10).

To test intracellular RNA replication, cells were transfected by electroporation or infected at the MOIs indicated in the figure legends with packaged replicons or viruses and virus-specific RNAs were labeled with [$^3$H]uridine as described in the figure legends. RNAs were isolated from the cells by TRIzol reagent, as recommended by the manufacturer (Gibco-BRL, Bethesda, Md.), denatured with glyoxal in dimethyl sulfoxide and analyzed by agarose gel electrophoresis.

Development of EEE and VEE Replicon-Containing Cell Lines Expressing Alkaline Phosphatase Four micrograms of in vitro-synthesized RNAs were transfected into 5×10$^6$ BHK-21 cells. Different aliquots of electroporated cells were seeded into 100-mm tissue culture dishes. For the selection of Pur$^r$ cells, puromycin was added to the media at 24 h postelectroporation. Colonies of Pur$^r$ cells were randomly selected and expanded and stocks of the cells were used for a second selection of Pur$^r$ colonies and further propagation. This additional cell cloning was expected to make a more homogeneous cell population. Alkaline phosphatase activity in the media was measured using a Great EscAPe SEAP detection kit (BD Biosciences) according to the manufacturer's instructions.

Identification of the Adaptive Mutations in VEE Replicons

Four micrograms of in vitro-synthesized RNAs were transfected into 5×10$^6$ Huh-7 cells. Cells were seeded into 100-mm tissue culture dishes, and Pur$^r$ colonies were selected for 2 weeks. Total RNA was isolated from all of the expanded colonies and the amount equivalent to 10 Pur$^r$ cells was transfected into Huh-7 followed by selection in the presence of puromycin. RNA was isolated from three randomly selected Pur$^r$ cell clones and RNAs were isolated by TRIzol using the procedure recommended by the manufacturer (Invitrogen). Overlapping fragments approximately 1,000 nt long were synthesized by using VEE TC-83-specific primers with a minimal number of cycles applied, usually between 15 and 20 cycles of PCR.

After purification on agarose gels, fragments were sequenced without cloning. Mutation-containing fragments were cloned into pRS2, an analog of pUC19, sequenced to confirm the consensus sequence and cloned into a 5'VEErep/Pac genome to confirm their effect on the replication of VEE-specific RNAs. DNA fragments representing the 5' terminal sequence of virus isolates were synthesized using a commercially available FirstChoice RLM-rapid amplification of cDNA ends kit according to the procedures recommended by the manufacturer (Ambion). Fragments were purified by agarose gel electrophoresis and cloned into the plasmid pRS2. Multiple, independent clones were sequenced to determine variations in the 5' ends of the genomes.

Analysis of Protein Synthesis

BHK-21 cells were seeded into 35-mm dishes at a concentration of 5×10$^5$ cells/well. After 4 h incubation at 37° C. in 5% CO$_2$ they were infected at an MOI of 10 PFU/cell with the viruses indicated in the figure legend, in 500 μl of alpha MEM supplemented with 1% FBS at room temperature for 1 h with continuous shaking. The medium was then replaced by corresponding complete medium and incubation continued at 37° C. At the indicated times post infection, the cells were washed three times with phosphate-buffered saline (PBS) and then incubated for 30 minutes at 37° C. in 0.8 ml of DMEM medium lacking methionine, supplemented with 0.1% FBS and 20 μCi/ml of [$^{35}$S]methionine. After this incubation, cells were scraped into the media, pelleted by centrifugation and dissolved in 200 μl of standard protein loading buffer. Equal amounts of proteins were loaded onto sodium dodecyl sulfate-10% polyacrylamide gels. After electrophoresis, gels were dried, autoradiographed and analyzed on a Storm 860 PhosphorImager (Molecular Dynamics).

EXAMPLE 2

Venezuelan Equine Encephalitis Virus Replicons are Less Cytopathic Compared to Sindbis Virus-Based Constructs In order to compare the in vitro replication of VEE and EEE replicons with similar SIN-based (SINrep) constructs (10), cDNA copies of both replicons were created in low-copy-number plasmids. The use of low-copy-number plasmids made replicon- and entire viral genome-coding plasmids stable during propagation in *Escherichia coli*. Original cloned genetic material from the Venezuelan equine encephalitis virus TC-83 strain and EEE North American strain Florida 91 was recloned under control of the SP6 promoters into a pToto1101 plasmid to replace the SIN genome. The final constructs contained the 5' and 3' cis-acting elements required for replication, the nsP1 to nsP4 genes and the selectable marker Pac gene cloned under control of viral subgenomic promoters (FIG. 1).

Two variants of the VEE replicon were generated. One of these (VEErep/Pac) contained the TC-83-derived 5' UTR followed by TC-83 nonstructural proteins, whereas the second variant, 5'VEErep/Pac, differed in a single position: the adenine in the third position of the 5' UTR was replaced by guanine. This mutation made the replicon's 5' UTR identical to that found in the epizootic, highly pathogenic VEE TRD strain. The mutation in this position was previously shown to play a critical role in determining the interferon sensitivity of VEE (5, 14). Equal amounts of the in vitro synthesized replicons' RNAs, between 1 and 4 μg in different experiments, were transfected into BHK-21 cells, and 24 h later, selection with puromycin was applied. The previously described noncytopathic SINrep/L/Pac replicon (8) (with the nsP2 P726.3L mutation) and cytopathic, wt SIN replicon SINrep/Pac were used in these experiments as reference contro ls for comparing the efficiencies of Purr colony formation.

Surprisingly, this assay revealed that both VEE- and EEE-based replicons easily established persistent replication. EEErep/Pac formed Pur$^r$ colonies with an efficiency similar to that found for the mutated SIN replicon SINrep/L/Pac. The replicon-containing cells had the same morphology as naive BHK-21 cells and demonstrated similar growth rates (FIG. 1 and data not shown). Also, it was demonstrated that compared to EEErep/Pac, the VEErep/Pac replicon was noticeably more cytopathic and between 10- and 20-fold fewer cells formed Pur$^r$ colonies. At the early time point, within 1 to 2 days after transfection with VEErep/Pac, all of the cells were Pur$^r$, but the majority of them eventually died within the next few days, most likely due to changes in cell metabolism caused by the replication of virus-specific RNAs. The surviving cells exhibited morphological changes and slower growth (FIG. 1).

The TRD-specific single point mutation in the 5' UTR of 5'VEErep/Pac (A33G) (5) was critical for the noncytopathic phenotype of the VEE replicon. This single nucleotide change decreased the cytopathicity of the 5'VEE replicon, reduced its negative effect on cell growth (compare the sizes of colonies in FIG. 1) and strongly increased the efficiency of forming Pur$^r$ colonies to the level of noncytopathic SINrep/L/Pac or EEErep/Pac. The control SINrep/Pac replicon, containing nonstructural genes derived from wt SIN, was highly cytopathic and formed Pur$^r$ foci 5 orders of magnitude less efficiently than both EEErep/Pac and 5'VEErep/Pac constructs of fewer than 10 colonies of Purr cells per μg of transfected RNA).

Taken together, the results indicated that, compared to wt SIN- and wt SFV-derived constructs (15-18), replication of EEE- and VEE-based replicons was less cytopathic. The latter replicons were capable of establishing persistent replication in a high percentage of transfected BHK-21 cells. In addition, the replacement of A3 by G in the 5' UTR of the Venezuelan equine encephalitis virus TC-83-based replicon had a strong impact on its ability to persistently replicate in the BHK-21 cell line.

EXAMPLE 3

Replication of Venezuelan Equine Encephalitis Virus-Based Replicons

To compare the efficiencies of RNA replication, 4 μg of each replicon (5'VEErep/Pac, VEErep/Pac, EEErep/Pac, SINrep/Pac, and SINrep/L/Pac) was transfected into BHK-21 cells. The RNA replication and transcription of the subgenomic, Pac-encoding RNA was tested by metabolic RNA labeling with [$^3$H]uridine in the presence of dactinomycin, both between 4 and 8 h posttransfection and after a few passages of the Purr cells. RNAs were isolated, denatured, resolved by gel electrophoresis, and detected by autoradiography.

Venezuelan equine encephalitis virus and EEE replicons demonstrated high levels of replication of the genome RNAs and transcription of the subgenomes (FIG. 2A) at between 4 and 8 h postelectroporation. At this time point, they replicated fivefold less efficiently than did SINrep/Pac but dramatically better than the noncytopathic SINrep/L/Pac, whose RNAs could be visualized only after 10-fold-longer exposure of the film or by metabolic labeling of the RNA after superinfection with the wt SIN virus, whose replicative machinery performed additional RNA amplification (data not shown). All of the SINrep/Pac-transfected cells and a large fraction of cells transfected with VEErep/Pac developed profound morphological changes and died within the next 48 h. The surviving cells continued to support the replication of VEErep/Pac, 5'VEErep/Pac, and EEErep/Pac RNAs. They were resistant to puromycin and capable of growth.

After a few passages, RNA replication became at least 10-fold lower than after electroporation (FIG. 2B), indicating that persistent replication was most likely associated with a lower level of viral nonstructural proteins and replicative complexes present in the cells. During both the initial (acute) and persistent phases, no significant differences were detected between the replication levels of VEErep/Pac and 5'VEErep/Pac RNAs, but as described above, they displayed significant differences in the ability to cause CPE that were likely a result of the mutation in the 5' UTR. The same mutation had a pronounced effect on transcription of the subgenomic RNA, with the VEE TRDspecific sequence of the 5' UTR leading to a higher level of subgenome synthesis. This difference in transcription of the subgenomic RNA suggested that the balance between replication and transcription could be determined, in part, by competition for the RdRp between the 3' end and subgenomic promoters in the minus-strand intermediate.

The low cytotoxicity of the VEE- and EEE-derived replicons, compared to wt SIN constructs (8, 10, 19), was an unexpected phenomenon. Thus, to rule out the possibility that this was not a result of spontaneous mutations introduced during cloning procedures, the Pac gene in the 5'VEErep/Pac construct was replaced by SIN structural genes. The 5'VEE/SIN chimera was constructed instead of VEE TC-83 virus with the (A33G) mutation in the 5' UTR, because this chimeric virus was not pathogenic for mice of any age after either intracutaneous or subcutaneous inoculation and could be used in BSL2 conditions, while VEE TC-83 with the mutated 5' UTR required BSL3-plus conditions due to a strong positive effect of the 5' UTR mutation on virus pathogenicity (5, 14, 20).

Figure 3A:
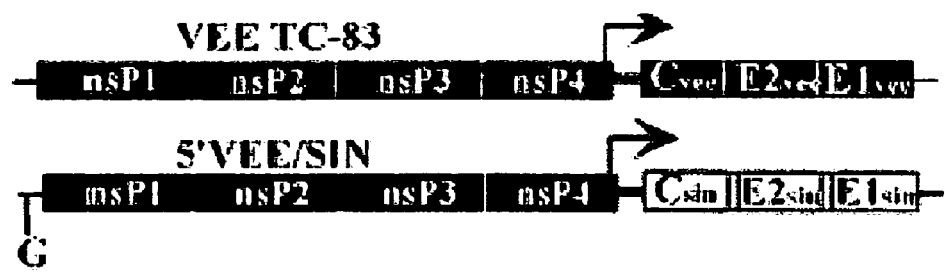
FIGS. 3A-3B depict a schematic representation of viral genomes and analysis of virus growth.
Figure 3B:
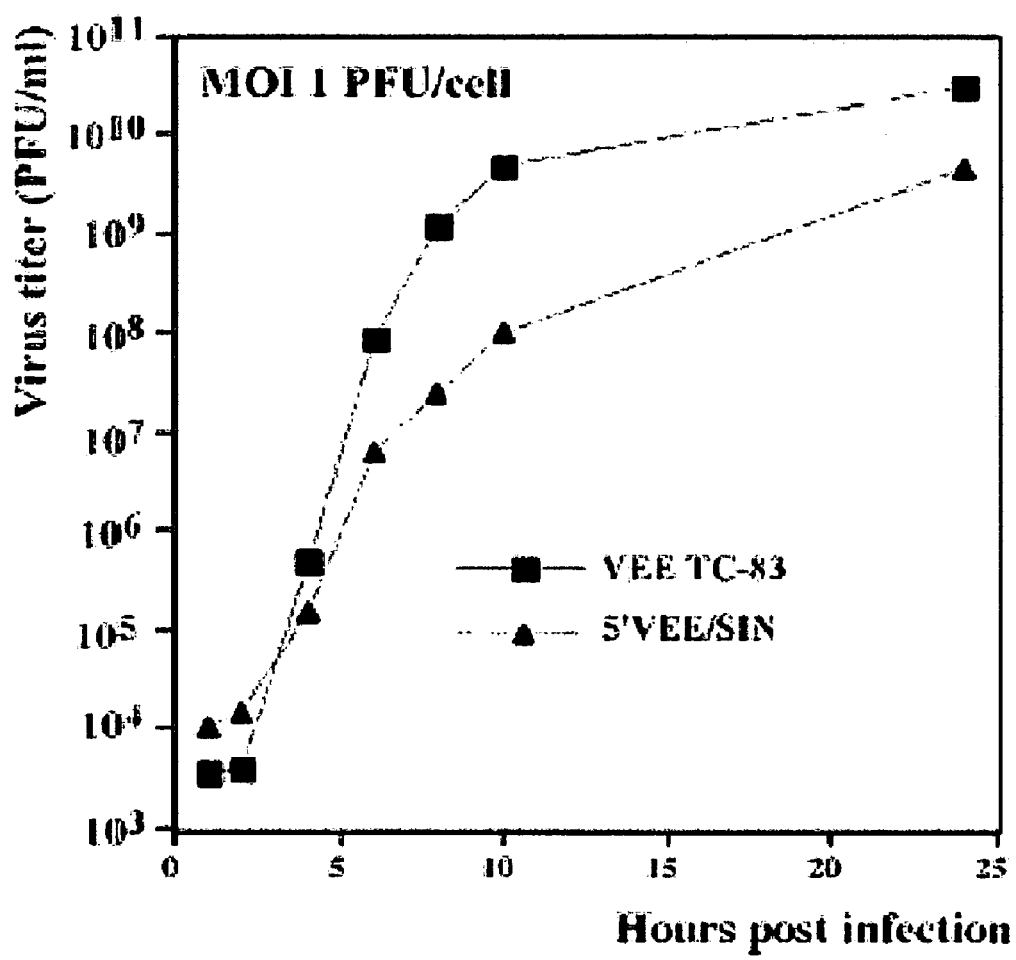

EEE/SIN chimeras were not tested for two reasons. First, the replication level of EEErep/Pac was very similar to that found for 5'VEErep/Pac. Second, there were safety concerns about creating the EEE/SIN chimera because of the possibility of recreating a WEE-like virus that would also require a higher biosafety containment. The in vitro-synthesized 5'VEE/SIN RNA exhibited the same infectivity (PFU/μg of RNA) as control SIN Toto1101 RNA in the infectious center assay (data not shown), indicating that no mutations were required for virus viability and for making it capable of causing CPE. The chimeric virus caused plaque formation and was capable of efficient growth in BHK-21 cells, but it replicated to noticeably lower final titers than plasmid-derived VEE TC-83 (FIGS. 3A-3B). Thus, lower cytopathicity is a natural feature of VEE TC-83-based replicons with a TRD-derived 5' UTR, and the same RNA replication level was sufficient for virus production and plaque formation.

EXAMPLE 4

Figure 4A:
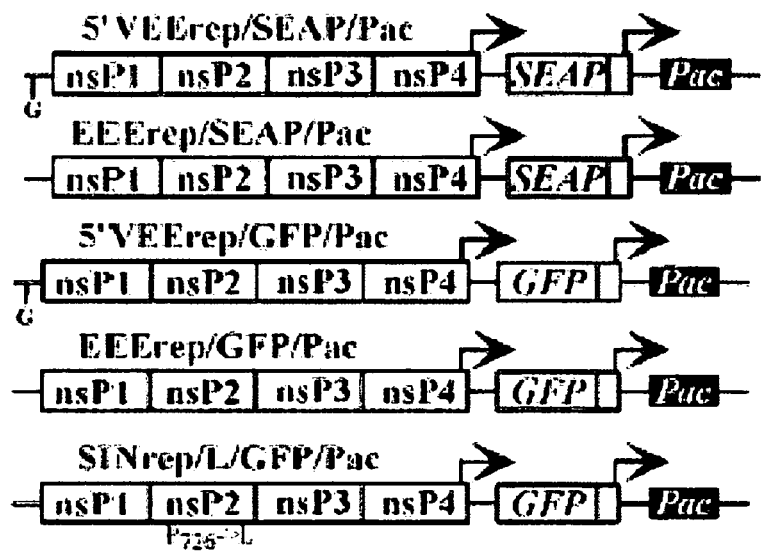
FIGS. 4A-4C depict a schematic representation of the double subgenomic replicons expressing Pac and GFP or SEAP and analysis of protein expression.
Figure 4B:
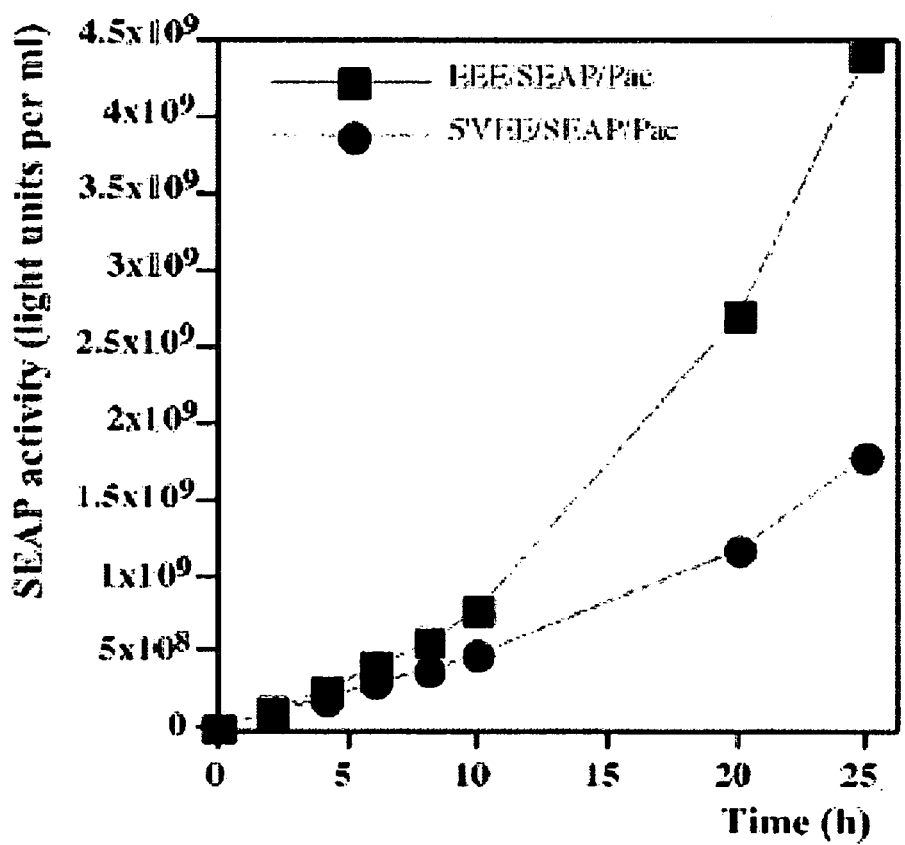

Venezuelan Equine Encephalitis Virus Replicon-Containing Cells can be Used for Stable Production of Heterologous Proteins Considering the need to develop cell lines for screening the antiviral drugs capable of downregulating the replication of VEE and EEE, a double subgenomic replicons expressing the selectable marker gene (Pac) and either a gene of secreted alkaline phosphatase (SEAP) or a GFP-encoding gene were designed (FIG. 4A). Stable Pur$^r$ cell lines expressing SEAP or GFP were easily established after transfection of in vitro-synthesized RNAs into BHK-21 cells. 5'VEErep/SEAP/Pac- and EEErep/SEAP/Pac-containing cells secreted SEAP at rates of 50 and 100 ng/106 cells/h, respectively (FIG. 4B). Secretion was not linear due to cell growth.

Figure 4C:
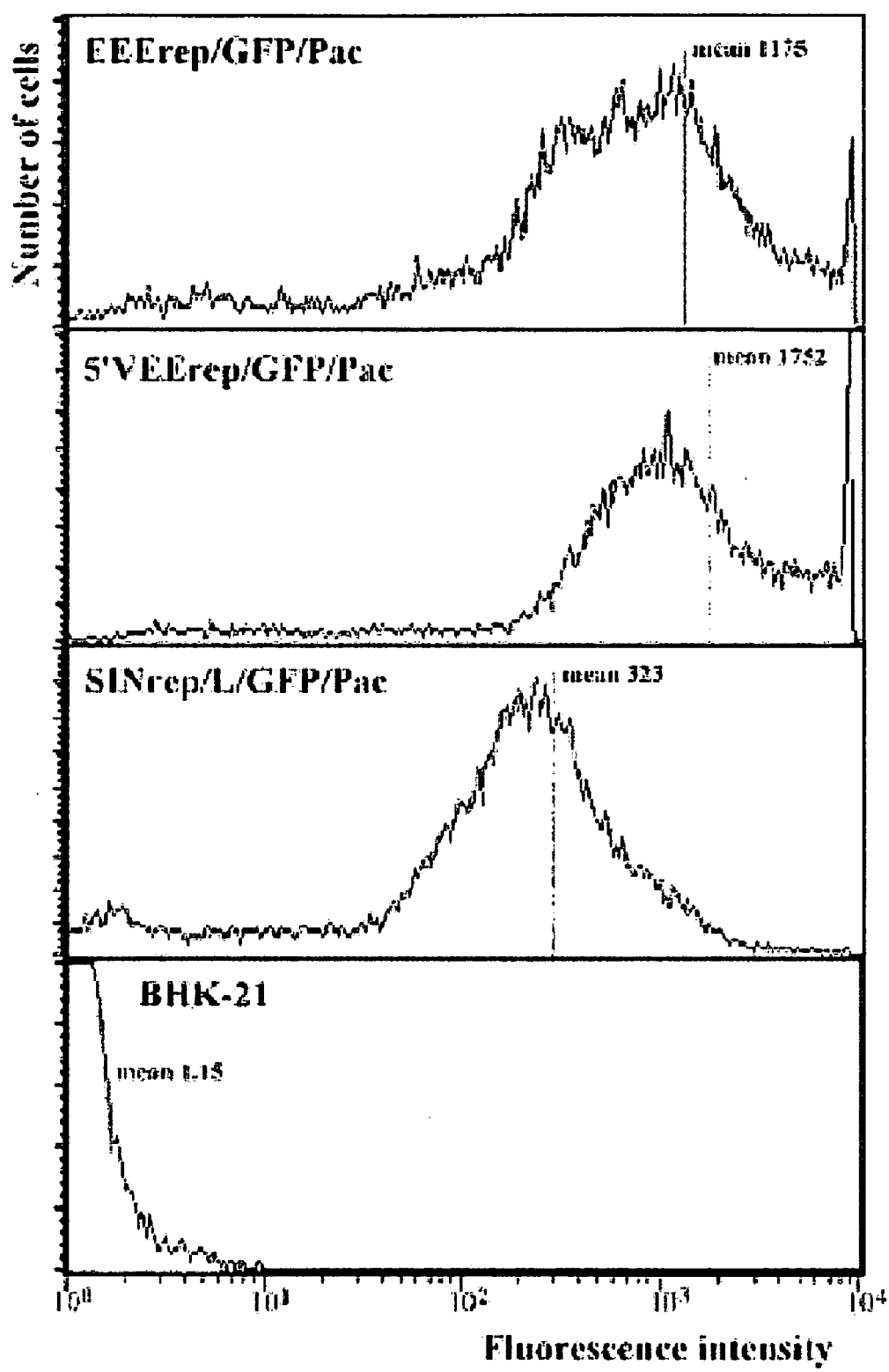

GFP expression was also readily detectable in the cells transfected by either VEErep/GFP/Pac or EEErep/GFP/Pac replicons. The expression appeared to be almost 10-fold higher than that found for the previously described noncytopathic SINrep/L/GFP/Pac replicon containing a P7263L mutation in nsP2 (FIGS. 4A and 4C). The stability of heterologous protein expression was tested by passaging the EEErep/GFP/Pac- and 5'VEErep/GFP/Pac-containing cells for 10 passages (using a 1:10 to 1:20 dilution at each passage). In the presence of puromycin, the percentage of GFP-negative cells did not noticeably increase and remained below 1 to 2% of the cell population (data not shown).

Figure 5:
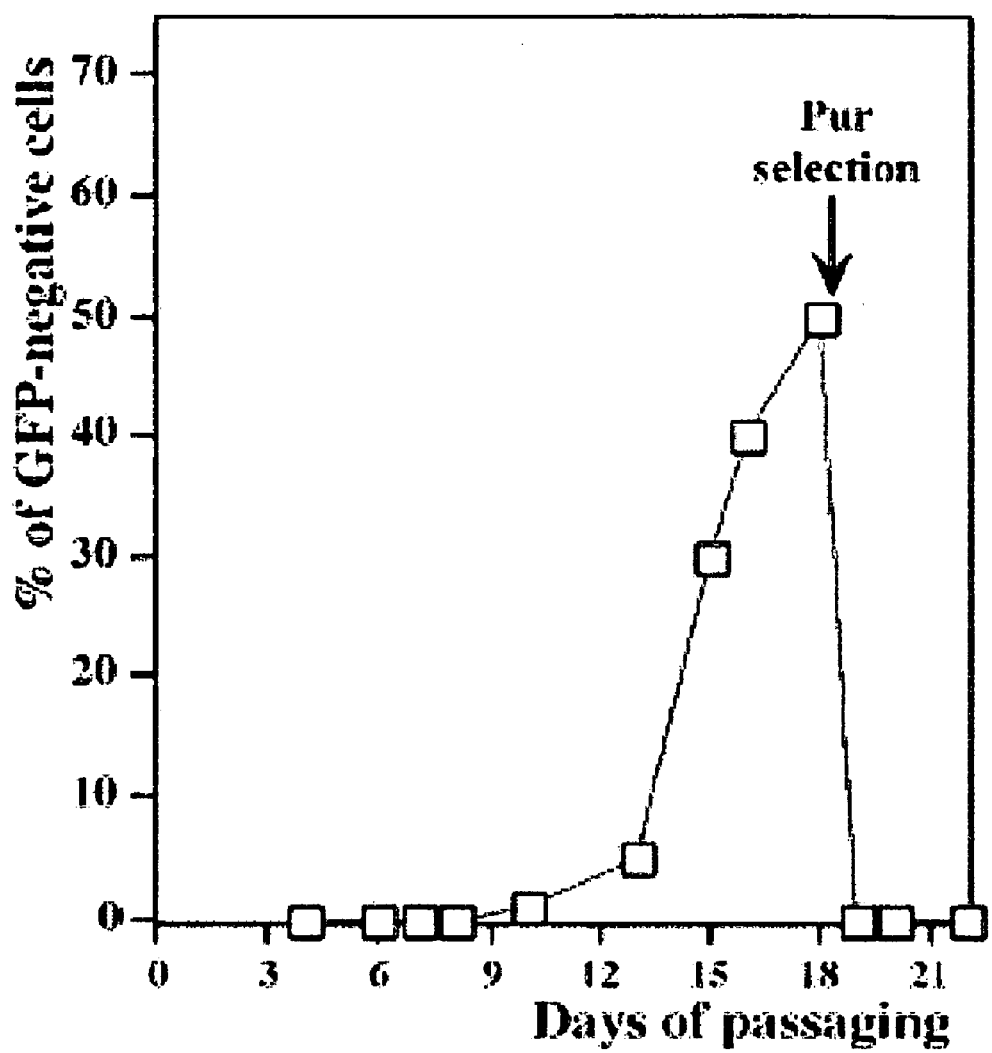
FIG. 5 depicts the stability of GFP expression by the persistently replicating EEErep/GFP/Pac replicon. Previously selected Pur$^r$ cells were passaged 1:10 approximately every 48 h in the absence of puromycin in the medium. At the indicated times the percentage of GFP-negative cells was calculated by examination of several random fields on the inverted fluorescent microscope. Puromycin was added back to the medium after 18 days of passaging in drug-free medium.

Passaging of the EEErep/GFP/Pac-containing cells in the absence of the drug caused an accumulation of GFP-negative cells. However, essentially all of these GFP-negative cells were sensitive to puromycin and died after reapplication of the drug (FIG. 5).

This was an indication that a GFP-negative phenotype was most likely a result of lower replication or complete loss of virus-specific RNAs in the absence of puromycin. However, the possibility of the efficient elimination of both Pac and GFP genes together cannot be completely ruled out. Both EEErep/GFP/Pac and 5'VEErep/GFP/Pac were also capable of persistent replication in mosquito C710 cells. Similar to BHK-21 cells, in the puromycin-containing media, C710 cells expressed GFP for at least 10 passages without noticeable accumulation of GFP-negative cells (data not shown).

EXAMPLE 5

Persistently Replicating Venezuelan Equine Encephalitis Virus RNAs do not Interfere with Replication of Heterologous Viruses VEE- and EEE-specific RNA replication in BHK-21 cells and the ability to express heterologous proteins suggested that they would be useful for gene expression and trans-complementation of defects in the replication of other viruses. One critical problem in the latter application could be the interference of the replication of the alphavirus-specific RNAs with the replication of other, particularly slower-replicating, viruses. To evaluate this type of interference, cells carrying 5'VEErep/Pac and EEErep/Pac replicons were infected with West Nile virus (WNV), the MP-12 strain of Rift Valley fever virus (RVFV) and different homologous and heterologous alphaviruses (FIGS. 6A-6D).

Both WNV and RVFV replicated in the replicon-containing cell lines as efficiently as in naive BHK-21 cells, thereby indicating that in this cell type, replication of VEE- and EEE-specific RNAs did not interfere with the replication of WNV and RVFV belonging to other families. Heterologous alphaviruses replicated in the 5'VEErep/Pac- and EEErep/Pac-containing cells as efficiently as in naïve BHK-21 cells. However, the replication of homologous viruses was detectably less effective. Growth rates and final titers of homologous viruses were 10- to 100-fold lower, indicating a significant level of interference caused by the replicons. These results correlated with data concerning the superinfection exclusion (21). Thus, in spite of more efficient replication than previously selected, noncytopathic, SIN-based constructs, VEE- and EEE-based replicons can be used for trans-complementation experiments with heterologous viruses, including other members of the alphavirus genus.

EXAMPLE 5

VEE Genome-Based Replicons can Accumulate Adaptive Mutations

As did SIN replicons, the VEE- and EEE-based constructs demonstrated an inability to establish persistent replication in cell lines that possessed no defects in IFN-α/β induction or signaling and that were capable of developing the antiviral response (data not shown). It has been demonstrated previously that SIN replicons with the adaptive mutations in nsP2 could replicate indefinitely in a very limited number of cell lines with known defects in IFN signaling. SIN with mutated nsP2 caused persistent infection in IFN-competent cells when grown in the presence of IFN-specific antibodies (8,22-23). The originally constructed VEErep/Pac, 5'VEErep/Pac, and EEErep/Pac had very similar ranges of cell types that supported persistent replication. However, after transfection of the Huh-7 cells with in vitro-synthesized 5'VEErep/Pac RNA, a very limited number (less than 50) of Pur$^r$ colonies were selected. This pool of cells resistant to puromycin was expanded and isolated total RNA was used to retransfect naïve Huh-7 cells. In spite of a low concentration of replicon-specific RNAs in this sample compared to the samples of the in vitro-synthesized replicon, foci of Pur$^r$ cells were readily selected after the repeated transfection.

These cell colonies were expected to contain replicons with adaptive mutations that would allow them to persistently replicate in the Huh-7 cells. The nonstructural genes and 5' UTR of RNAs obtained from three randomly selected, large colonies were sequenced to identify adaptive mutations. A single mutation was identified in each of the three RNAs: nsP2Q739L, nsP2P733S and nsP3 L121P (FIGS. 7A-7B). The rest of the nsP1-4 coding sequence and the 5' UTR in each cell clone-derived RNA was identical to the transfected RNA (5). Interestingly, application of the same selection method to VEErep/Pac and EEErep/Pac replicons was unsuccessful. Both replicons transfected Huh-7 cells equally efficiently and made initially virtually 100% of cells resistant to puromycin.

However, transfections of Huh-7 cells with EEErep/Pac made cells incapable of growth and all of them were dead within the next 2 weeks of selection. In repeated transfection experiments, a few foci of Huh-7 cells with persistently replicating VEErep/Pac were selected, but these likely adapted replicons were present in the cells at very low concentrations. Compared to 5'VEErep/Pac-containing cells, at least 10 more PCR cycles were required to detect VEE-specific sequences in cells transfected with VEErep/Pac and these replicons were not further investigated.

Despite more than four orders of magnitude higher efficiency of Pur$^r$ colony formation activity in BHK-21 cells than Huh-7 cells, the possibility was still considered that the 5'VEErep/Pac replicon required adaptive mutations for persistent replication in both cell lines. To test this, a population of 5'VEErep/Pac-carrying cells was cloned after 2 weeks postelectroporation and replicons from three randomly selected colonies were sequenced. No mutations were detected in all of the nonstructural genes or the 5' UTR of the 5'VEErep/Pac replicons persisting in BHK-21 cells. Taken together, the data indicated that the mutations in the replicons were required only for persistence in IFN-α/β-competent Huh-7 cells and that they accumulated more efficiently in the VEE replicons than in the EEE-derived ones.

Figures 8A, 8B:
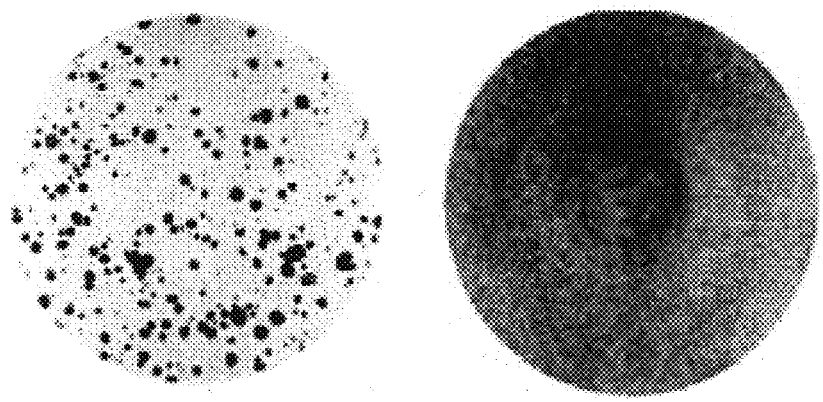
FIGS. 8A-8D depict an analysis of replicons' efficiency to persistently replicate in different cell lines.

The amino acid substitutions detected in 5'VEErep/Pac nsP2 were located close in primary sequence to mutated loci that was previously described for SIN replicons with reduced abilities to cause CPE in BHK-21 cells (8,24). These 5'VEErep/Pac nsP2 mutations were additionally investigated. Both mutations found were transferred into 5'VEErep/Pac (named 5'VEErep/S/Pac and 5'VEErep/L/Pac) and Huh-7 cells were transfected by in vitro-synthesized RNAs (FIG. 8A). In contrast to the original 5'VEErep/Pac, which was capable of forming very few foci during puromycin selection, electroporation of either 5'VEErep/S/Pac or 5'VEErep/L/Pac replicons made all of the cells drug resistant (FIG. 8B). No differences in the growth of the replicon-transfected cells and untransfected Huh-7 cells propagated in puromycin-free medium were detected and did not observe replicon-induced changes in cell morphology was not observed.

Figure 8D:
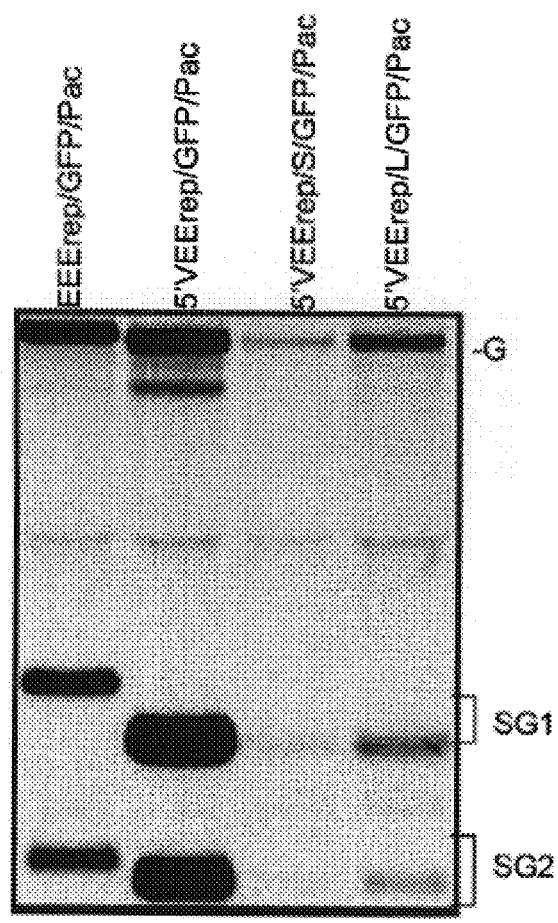
Figure 8C:
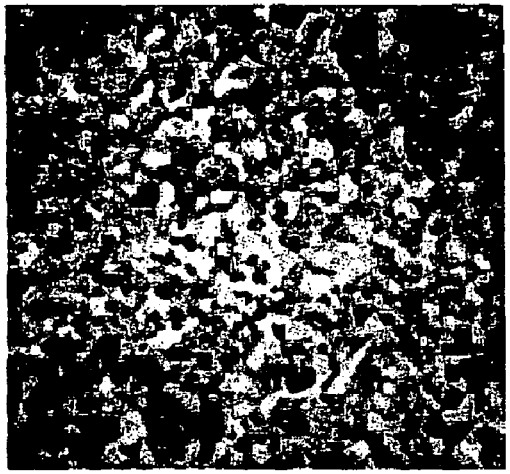
Figure 8C:
Figure 8C:
Figure 8C:
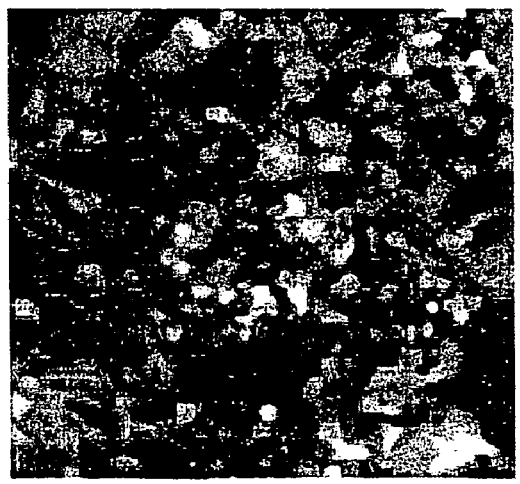

Another group of experiments was performed with 5'VEErep-based replicons expressing GFP and containing the adaptive mutations described above (5'VEErep/S/GFP/Pac and 5'VEErep/L/GFP/Pac). In contrast to the originally designed 5'VEErep/GFP/Pac, both constructs were capable of persistent replication and retained the ability to express high levels of heterologous protein (GFP), not only in BHK-21 cells, but also in Huh-7, HeLa, and NIH 3T3 cells (FIG. 8C). Replicons with the introduced mutations demonstrated 5- to 10-fold-lower levels of replication than the parental construct 5'VEErep/Pac (FIG. 8D), suggesting that their noncytopathic phenotype could be at least partially explained by less efficient replication and/or less efficient production of viral nonstructural proteins in the transfected cells. During the first 24 to 48 h postelectroporation, the originally constructed 5'VEErep/GFP/Pac replicon arrested cell growth and caused changes in cell morphology, but this was not the case when the transfections were performed using replicons with the adaptive mutations in nsP2. Thus, 5'VEErep-derived constructs with mutated nsP2 have the ability to persist in a number of cell lines other than BHK-21 cells and accordingly may be useful in a variety of trans-complementation experiments.

EXAMPLE 6

Packaging of VEE Replicons using DH RNAs with Deletion of All of the Nonstructural Genes The VEE replicon was designed on the basis of the vaccine strain VEE TC-83 genome (25). The only modification in the TC-83-specific sequence was a replacement of adenosine in the third position of the 5' UTR by guanosine that is present in the wild type (wt) Trinidad donkey (TRD) strain of VEE. The GFP-encoding sequence was cloned under control of the subgenomic promoter, the second subgenomic promoter drove the expression of puromycin acetyltransferase (Pur). GFP expression was convenient for evaluating the titers of packaged replicons in infectious units (inf.u), Pac expression was used for generating stable $Pur^R$ cell lines and measuring the titers in the colony-forming units (CFU). The previously designed SIN-based replicon SINrep/GFP (26) demonstrated a cytopathic phenotype and contained a single subgenomic promoter that controlled transcription of GFP-encoding subgenomic RNA.

The initially constructed VEE DH RNA cassettes (Hvee/C+GI, Hvee/C and Hvee/GI) (FIG. 9A) had a design similar to that previously described for SIN, VEE and SFV helpers (10, 27-28) in that the VEE genome fragment between nt 520 and 7290, encoding all of the nonstructural genes, was deleted. The subgenomic RNA of Hvee/C+GI contained all of the VEE structural genes and the Hvee/C and Hvee/GI helpers were capable of expressing only capsid and glycoproteins, respectively. The subgenomic RNA in Hvee/GI cassette encoded the VEE capsid with a deleted cluster of positively charged amino acids.

As with the SIN capsid-coding sequence, it is contemplated that the VEE capsid gene could contain a translational enhancer (19), which would increase the level of synthesis of viral structural proteins in the infected cells, in which the cellular protein synthesis would be significantly downregulated due to virus replication. Thus, the putative enhancer-containing sequence was left upstream of the glycoprotein genes. The deletion was aimed to make the capsid expressed from Hvee/GI incapable of RNA packaging and to eliminate a possibility of infectious viral genome formation after recombination between the VEE replicon and Hvee/GI helper. SIN-specific Hsin/C+GI and tRNA/Hsin/C+GI helpers have been described (10). They contained a 6914 nt-long deletion in the nonstructural genes and differed only in the 5'UTR. Hsin/C+GI had a natural SIN 5'UTR, while tRNA/Hsin/C+GI contained a tRNA structure (Monroe and Schlesinger, 1983) that increased the level of its replication and served as a packaging signal (11, 29).

Figures 9A, 9B:
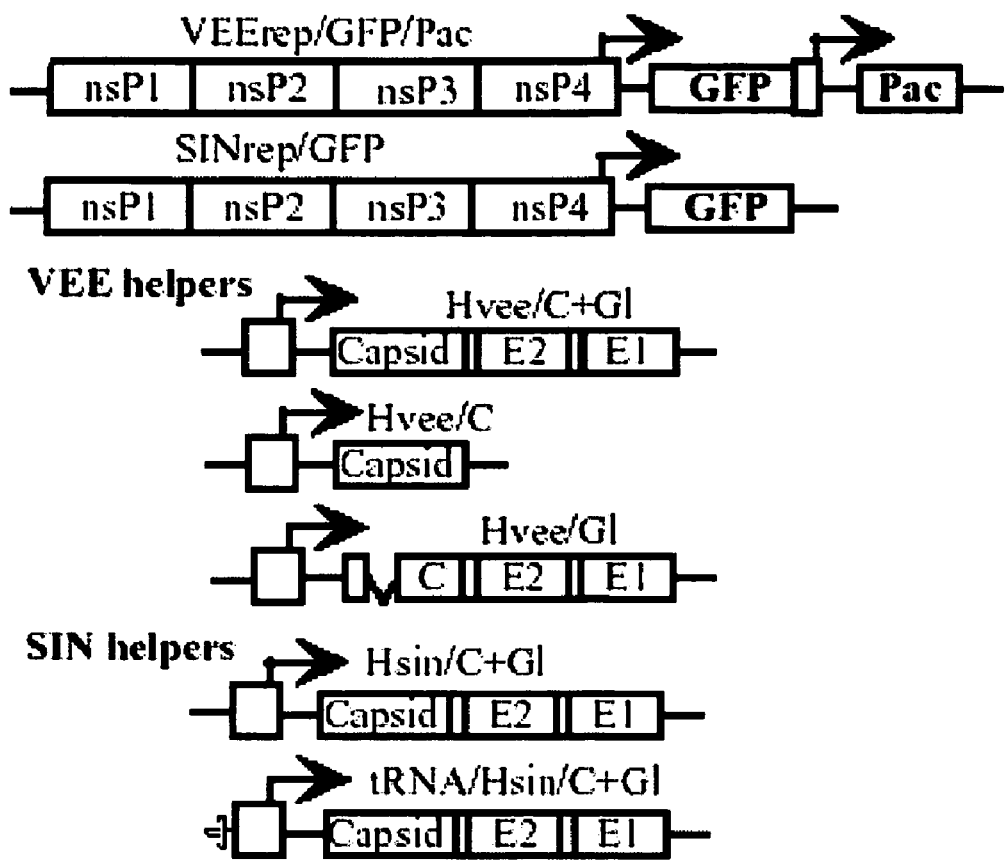
Figures 9C, 10:
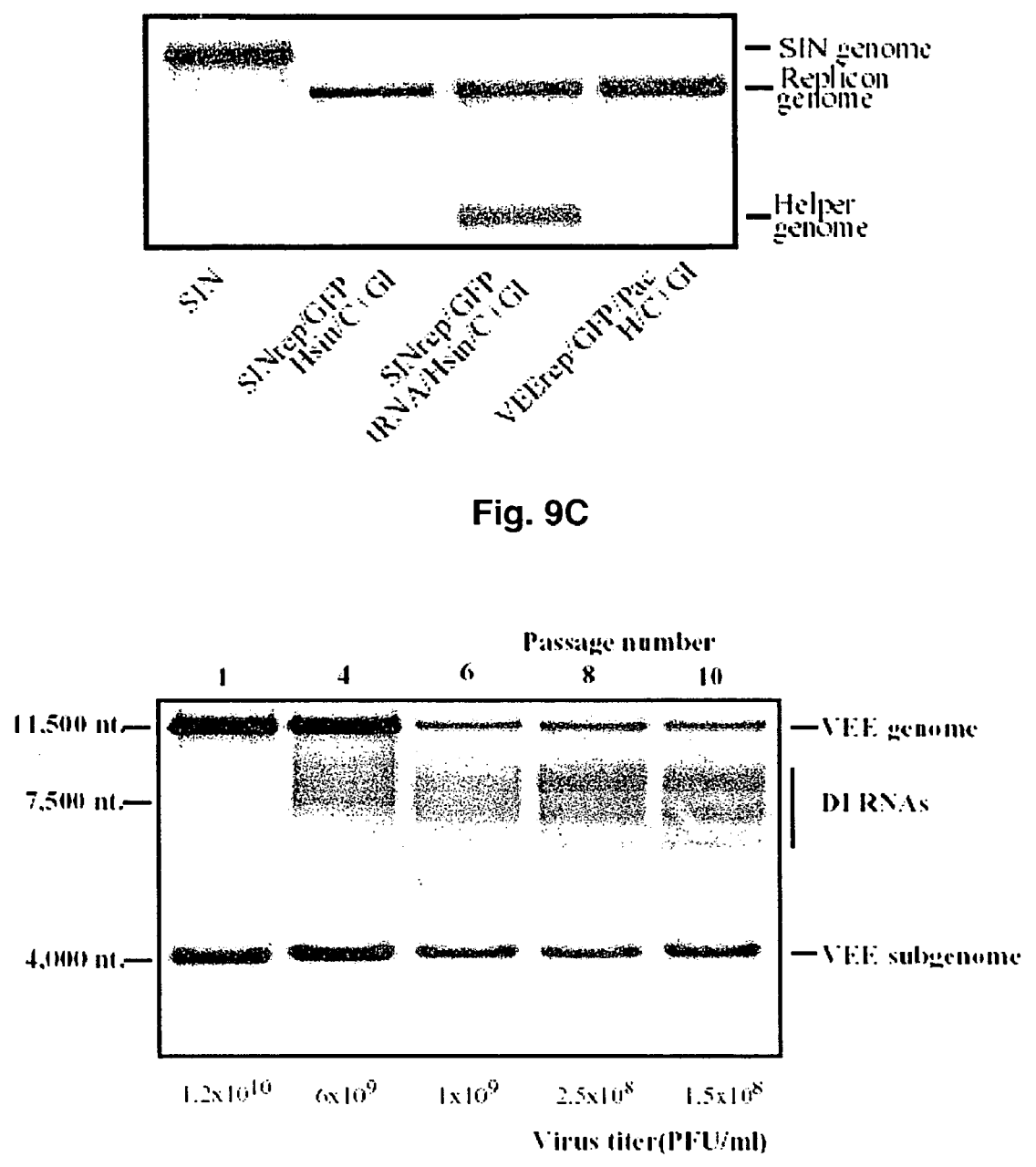
Figures 11A, 11B:
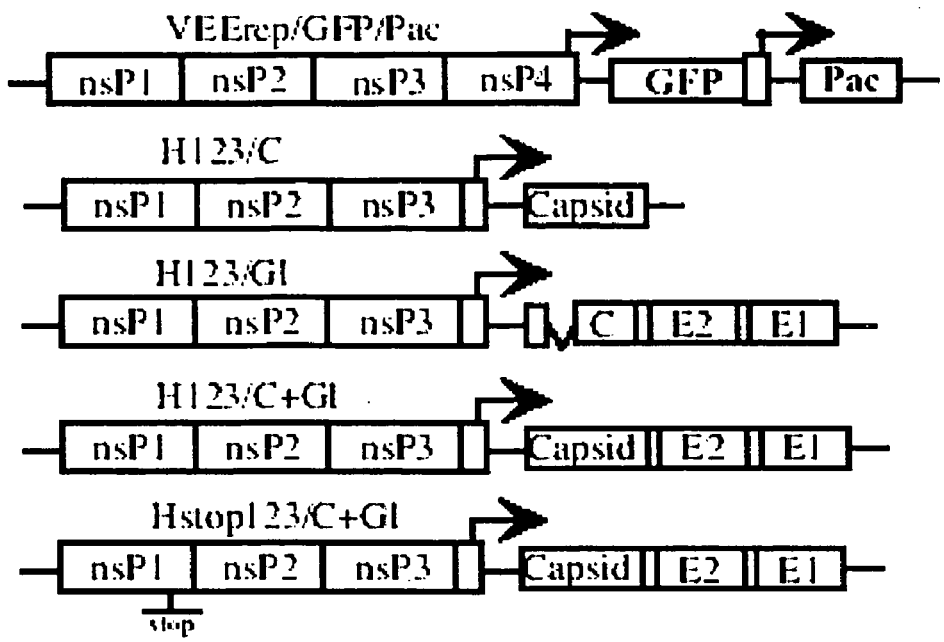
FIGS. 11A-11D depict packaging of Venezuelan equine encephalitis virus replicons in BHK-21 cells using helpers with deletions of nsP4-coding gene.
Figure 11C:
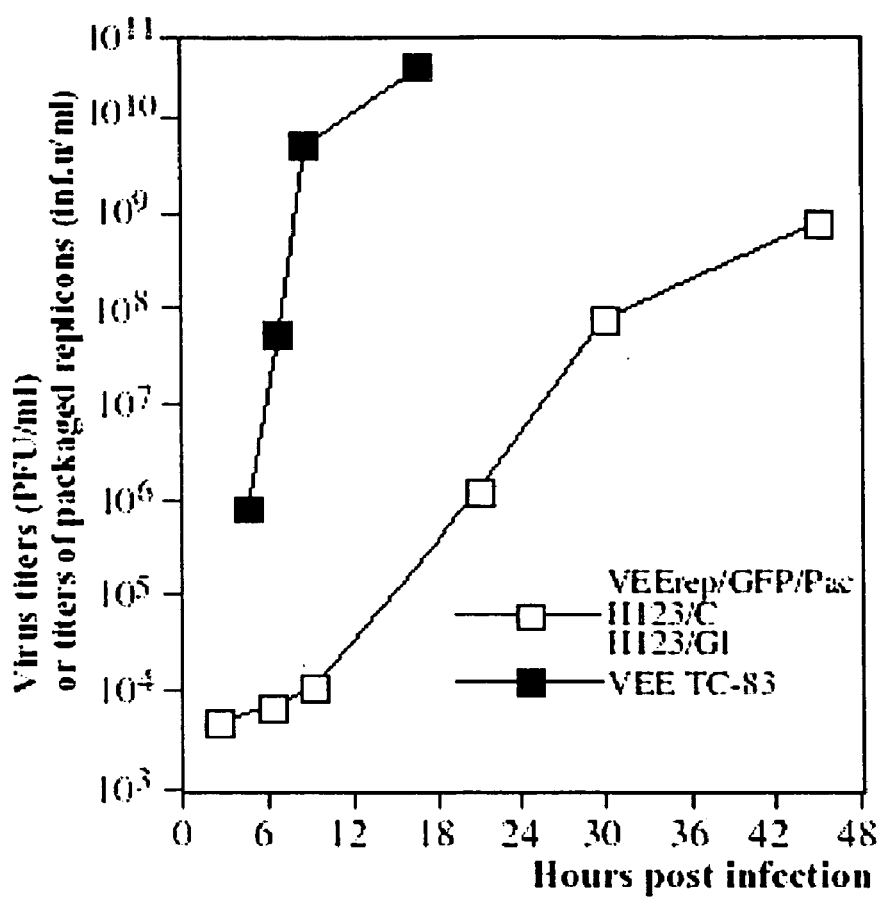
Figure 11D:
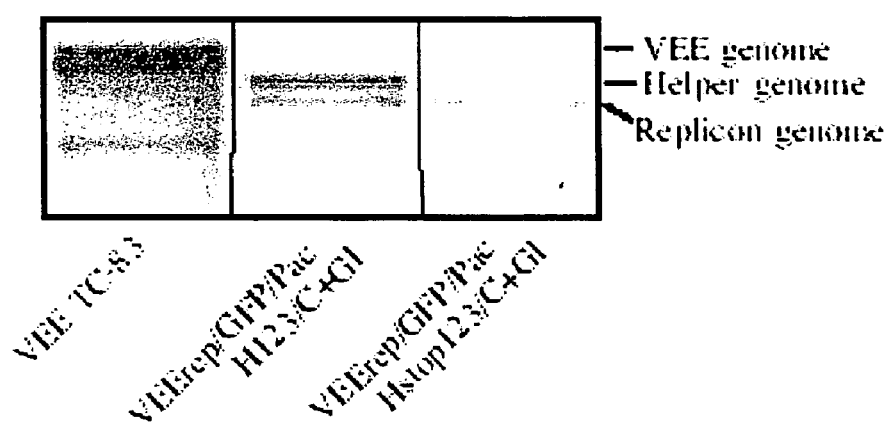

SIN and VEE replicons were transfected into BHK-21 cells together with the homologous helpers, indicated in FIG. 9A, and particles were harvested 24 h post electroporation, after development of profound cytopathic effect (CPE). VEE replicons were packaged very efficiently both by single helper Hvee/C+GI and by two helpers, Hvee/C and Hvee/GI, (FIG. 9B). In multiple experiments, titers of the replicon-containing particles reproducibly approached 1-2× $10^9$ inf.u/ml. Packaged VEE replicons were capable of establishing persistent replication and BHK-21 cells infected with replicons confirmed a $Pur^R$ phenotype and expressed GFP. The titers in CFU/ml were noticeably lower than titers in infectious units, but this was an expected phenomenon. As demonstrated herein, during the acute, early phase of replication, wt Venezuelan equine encephalitis virus replicons demonstrate some level of cytopathogenicity. Further passaging of Venezuelan equine encephalitis virus replicon-containing samples, aimed at testing the possibility of generating larger stocks, was inefficient. Hvee/C+GI helper genomes were present in released particles at low concentrations (FIG. 9C).

After infecting naïve cells by samples packaged with one or two helpers at an MOI of 10 inf.u/cell, the release of replicons only to the titer of 1-2×$10^7$ and 2.5×$10^6$ inf.u/ml, respectively, was detected. These titers were 2-3 orders of magnitude below the titers obtained after electroporation. There was no apparent difference when the infections were performed at higher MOIs (data not shown). The titers described here for VEE helpers were consistent with those obtained for SINrep/GFP packaged with Hsin/C+GI. The latter helper contained natural SIN 5'UTR, and it packaged a homologous SIN replicon very efficiently, but was incapable of self-packaging (FIG. 9C). Consequently, the samples could not be serially passaged at MOI of 10 inf.u/cell (FIG. 9B) or higher (data not shown) to produce titers exceeding $10^7$ inf.u/ml. Consistently, as demonstrated, a SIN helper with the 5'UTR derived from the naturally occurring DI RNA (tRNA/Hsin/C+GI) packaged not only the SIN replicon to high titers, but also packaged itself (FIGS. 9B-9C), making viral samples capable of being serially passaged without reductions in titers. Based on these data, it was assumed that concentrations of helper-containing particles in the samples of VEE replicons packaged with either Hvee/C+GI or Hvee/GI and Hvee/C were insufficient for delivery of helper RNAs into the cells at concentrations adequate for supporting next rounds of productive infection.

EXAMPLE 7

VEE DI RNAs

Alphavirus defective interfering RNAs are composed of i) cis-acting RNA elements required for their replication by replicative enzymes produced by replicating helper virus, and ii) the sequences that promote DI RNA packaging into viral particles, PSs (2). Structure of the DI RNAs was intensively studied for SFV and SIN (30-33), but there was no available information about the replication and sequences of VEE-specific DI RNAs. Thus, VEE DI RNAs were generated by serial passaging of cDNA-derived VEE TC-83 in BHK-21 cells at high MOIs.

The first passages were performed at an MOI of close to 10,000 PFU/cell. At the late passages, the MOI became lower (close to 100 PFU/cell) due to accumulation of the DI RNAs (FIG. 10). These RNAs were readily detectable by the metabolic labeling with [$^3$H]uridine, followed by electrophoresis in denaturing conditions. After 10 passages, there was no accumulation of clearly visible dominating DI RNA species and the DI RNAs genomes were distributed on the gels between 6,000 and 8,000 nt, albeit 1-3 diffuse RNA bands could be detected (FIG. 10). Based on the length of the VEE DI RNA genomes, it is contemplated that, as has been demonstrated for SIN and SFV, these DI RNAs contained a deletion of the viral structural genes, but, most likely, retained a major segment of RdRp-coding sequence.

To test this hypothesis, an RT-PCR analysis of VEE DI RNA genomes using primers specific to 3' UTR and nsP3 gene (nt 5312-5333) was performed. The PCR product was a diffuse band, containing DNA fragments ranging between 450 and 850 nt. After this material was cloned, 6 clones were selected at random that were shown to contain the end of the VEE nsP3 gene and fragments of nsP4 and 3' UTR of different lengths (data not shown). Thus, a significant fraction of the RNAs had a common feature: deletions of the structural genes and the nsP4-coding sequence. This was an indication that either i) the genome sequence between nt 520 and the end of nsP3 gene (deleted in Hvee helpers) could contain an efficient packaging signal(s) utilized by VEE capsid, or ii) the nonstructural protein(s) had to be expressed in cis from the DI RNA genomes to support the efficient persistence of the latter RNAs in the viral population, or iii) both the presence of PS and expression of nsPs cis could have synergistic positive effects on RNA packaging and/or replication.

EXAMPLE 8

Replication of VEE Helper RNAs Encoding nsP1-nsP3

To further investigate the effect of nsP1-nsP3-coding sequences on RNA packaging and the presence of virus-specific RNAs in viral populations, a set of recombinant helpers was designed that were either capable of expressing nsP1-3 (H123/C+GI, H123/GI and H123/C) or contained essentially the same nsP1-nsP3-coding nucleotide sequence except for an insertion of 4 nt at the 1620 position (Hstop123/C+GI). These few extra nucleotides destroyed the open reading in the nsP1-coding sequence, making this helper incapable of nsPs production. Helpers H123/C+GI encoded all of the VEE structural genes under control of the subgenomic promoter, and helpers H123/C and H123/GI contained VEE capsid- and glycoprotein-coding cassettes, respectively, that were the same as those described above for Hvee/GI and Hvee/C. Upon transfection into the cells, H123/C+GI efficiently packaged replicons to the titers exceeding $10^9$ inf.u/ml. Samples harvested after electroporation were passaged at an MOI of 10 and 1 inf.u/cell, and replicons were reproducibly packaged to a concentration of 1-2.5×$10^9$ inf.u/ml, indicating that helpers were present in the harvested samples at levels sufficient for supporting productive viral replication during serial passaging.

In the case of the two-helper packaging system (H123/C and H123/GI helpers), titers of packaged replicons were detectably lower, but during passaging at MOIs 10 and 1 inf.u/cell, remained at the levels exceeding $10^8$ inf.u/ml, which suggested that replicons and both helpers were efficiently packaged into viral particles. Harvested samples of replicons packaged with H123/C+GI or both H123/C and H123/GI helpers demonstrated plaque-forming activity, indicating the presence of the bi- and tri-partite genome particles, or aggregates of the particles, containing both replicon and helper genomes in the virions (11,34). However, the measured titers were 3 and 5 orders of magnitude lower for H123/C+GI or H123/C+H123/GI, respectively, than were titers determined in infectious units (data not shown). Thus, replicon and helper RNAs were predominantly packaged into separate virions. Compared to VEE TC-83, the tri-component genome virus with VEErep/GFP/Pac+H123/C+H123/GI genome demonstrated slower growth kinetics (FIG. 11C), but to comparable final titers. The Hstop123/C+GI helper was also efficient in replicon RNA packaging, but further passaging of the viral samples generated by electroporation was unsuccessful.

To additionally investigate if Hstop123/C+GI helper RNAs were packaged into virions, RNAs were metabolically labeled with $^{32}$P and the RNA content of purified viral particles was analyzed. After electroporation, Hstop123/C+GI helper genomes were packaged as efficiently as H123/C+GI RNAs (FIG. 11D). This result indicated that the nsP1-nsP3-coding sequence likely contained a packaging signal(s), that made both H123/C+GI and Hstop123/C+GI genomes more efficiently packaged into virions, when compared to the encapsidation of the Hvee/C+GI helper RNA that had the same 5' and 3' cis-acting RNA elements. These helpers demonstrated very similar levels of intracellular replication after co-transfection with replicons into the cells (data not shown). Nevertheless, at the next passage, the Hstop123/C+GI-containing viral populations were unable to establish productive replication, even at an MOI of 10 inf.u/cell, and replicon-containing infectious virions were released into the media to 3 orders of magnitude lower titers.

Taken together, the results indicated that possession of the packaging signal(s) and cis-acting promoter RNA elements are insufficient by themselves for the persistence of VEE-specific RNAs in a viral population. The ability of the RNAs to serve as a template for nsP1-nsP3 translation, in addition to being competent in utilizing the RdRp by the promoter sequences, appeared to play a critical role in replication and following packaging of defective VEE genomes.

EXAMPLE 9

Expression of nsP1, nsP2 and nsP3 in cis is Required for Persistence of VEE-Specific RNAs in Viral Populations To further investigate the phenomenon that synthesis of the nonstructural proteins in cis is beneficial for the persistence of VEE-specific RNAs in a viral population during serial passaging, whether synthesis of the entire P123 was required or if particular nsPs could be sufficient was tested. DH RNA capable of the production of only nsP1 could be easily designed (H1stop/C+GI), but the constructs capable of expressing only nsP2 or nsP3 had to have major changes in the DH genome sequence that would make interpretation of the data impossible. Therefore, new helpers were designed as three nearly identical cassettes (FIG. 12A): H123/C+GI, H1stop/C+GI and H12stop/C+GI had only 3-nt differences in the nsP-coding region. Thus, all of these DH constructs were expected to contain the same packaging signal(s).

As described above, H123/C+GI encoded the intact P123; H1stop/C+GI had an insertion of a stop codon immediately downstream of the nsP1-coding sequence. Similarly, a stop codon was inserted into the nsP2/nsP3 cleavage site of H12stop/C+GI, making this construct capable of P12, nsP1 and nsP2, but not nsP3, production. After co-electroporation of the replicon and newly designed helper RNAs into the cells, VEErep/GFP/Pac was efficiently packaged into infectious viral particles (FIGS. 12B-12C), and the DH H1stop/C+GI was the most efficient in replicon-containing particle production. All of the three helpers were found efficiently packaged into viral particles after co-electroporation with replicons (FIG. 12B). However, after the next passage at an MOI of 10 inf.u/cell, titers of packaged replicons were 2-3 orders of magnitude lower in H1stop/C+GI- and H12stop/C+GI-derived viral samples (FIG. 12C). In contrast, H123/C+GI was capable of supporting serial passaging without a decrease in titers (FIG. 12C).

These data indicated that nsP1-nsP3 expressed in cis (most likely in their unprocessed form P123) were critical for helper functioning in terms of its presence in the samples during serial passaging of packaged replicons and helpers in tissue culture. It cannot be completely ruled out as a possibility that the expression of nsP3 alone from the helper could be sufficient for supporting passaging. However, formation of the alphavirus replicative complexes is a sophisticated process, and it is difficult to expect proper nsP3 functioning when it is synthesized not in P123 context.

Figure 13A:
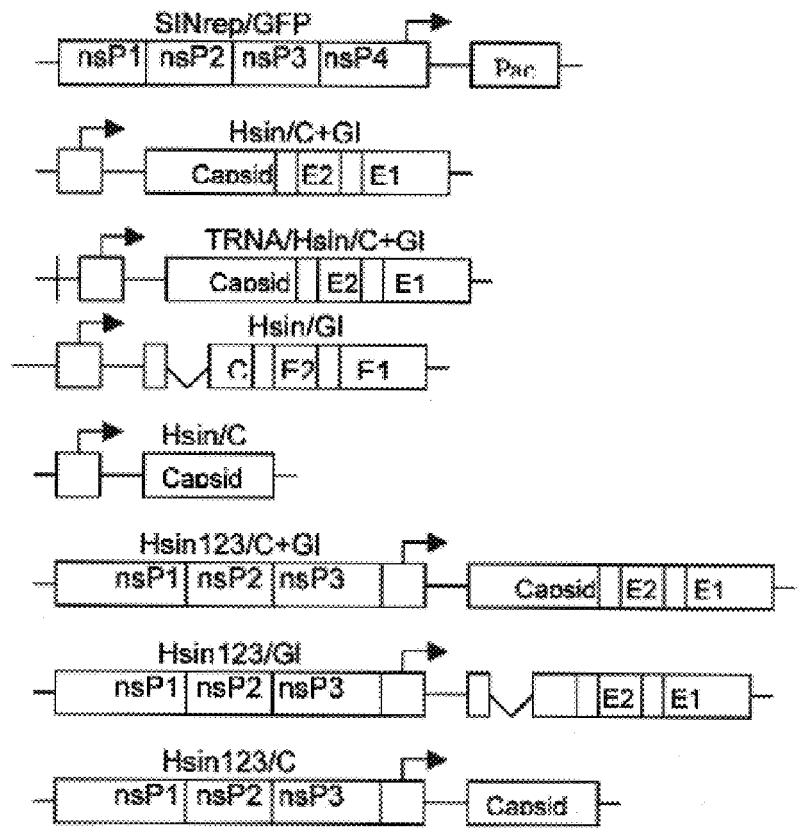
FIGS. 13A-13D depict packaging of SIN replicons in BHK-21 cells using helpers with deletions of the nsP4-coding gene.
Figure 13B:
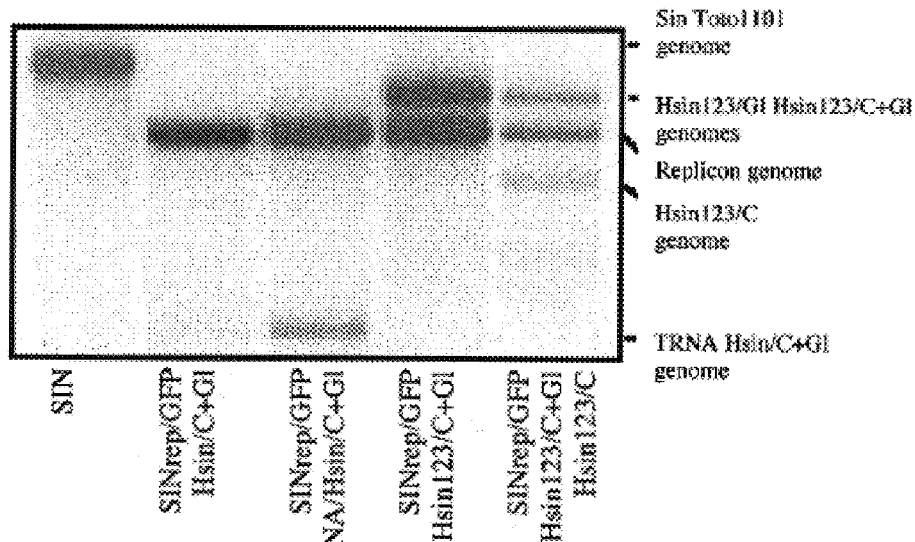
Figures 13C, 13D:
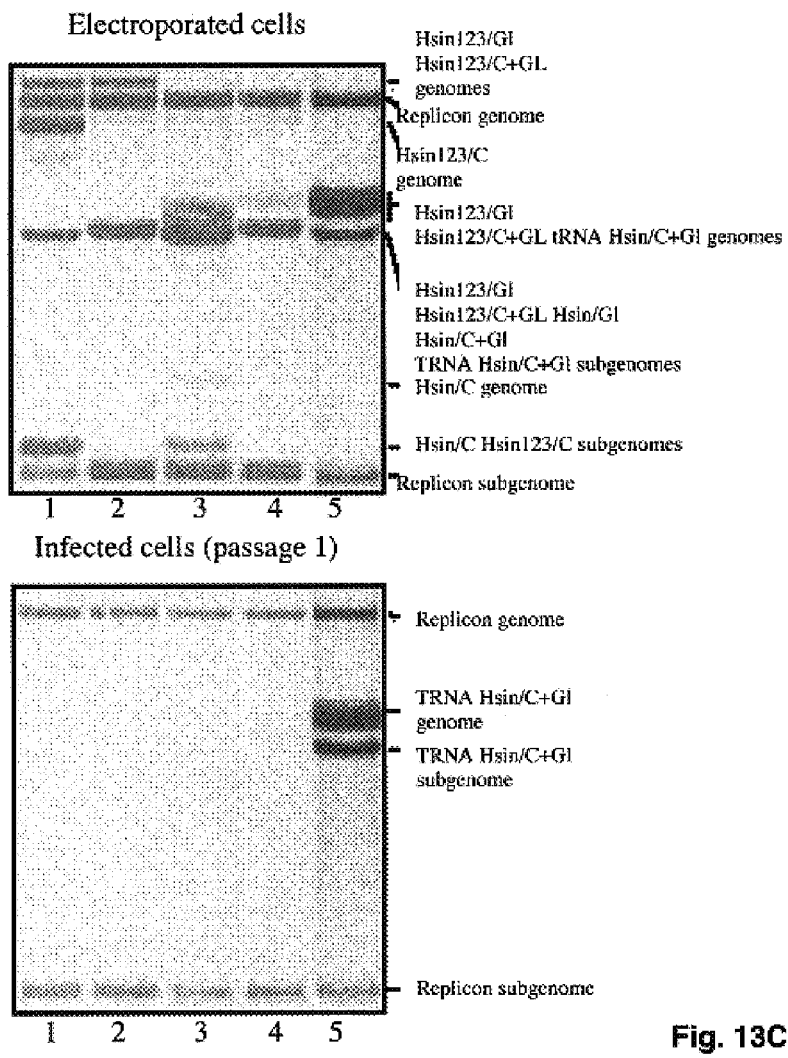

Interestingly, the requirement of nsP1-3 expression in cis for persistence of virus-specific RNAs in viral populations during serial passaging is a requisite of VEE, but not of SIN infection. A set of SIN helpers, Hsin123/C+GI, Hsin123/C and Hsin123/GI, were designed having essentially the same genome strategy as VEE-specific H123 constructs encoding nsP1-3 (FIG. 13A). After co-electroporation of SIN replicon and these helpers into BHK-21 cells, they were efficiently packaged into viral particles (FIG. 13B) and replicated in the transfected cells (FIG. 13C upper panel). However, at the next passage, their replication in the infected cells was below detectable levels, and only a control helper tRNA/Hsin/C+GI was replicating (FIG. 13C lower panel). As a result, titers of packaged replicons became 3 orders of magnitude lower than those after electroporation.

EXAMPLE 10

SIN and VEE Differ in the Efficiency of Infectious Virion Formation

Figure 14A:
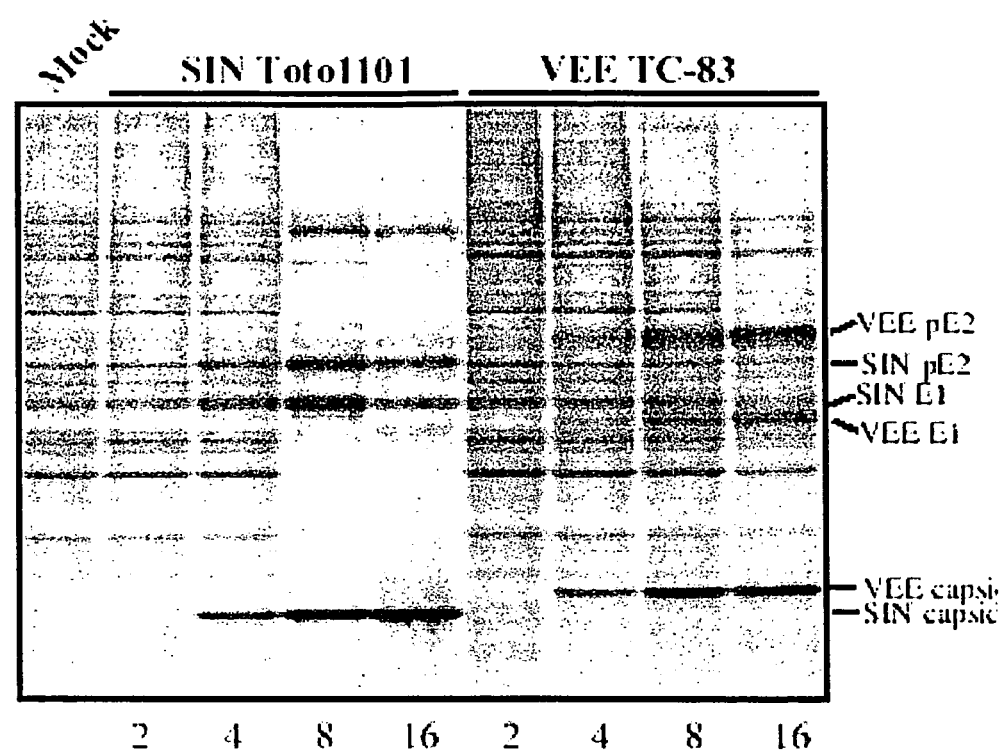
Figure 14B:
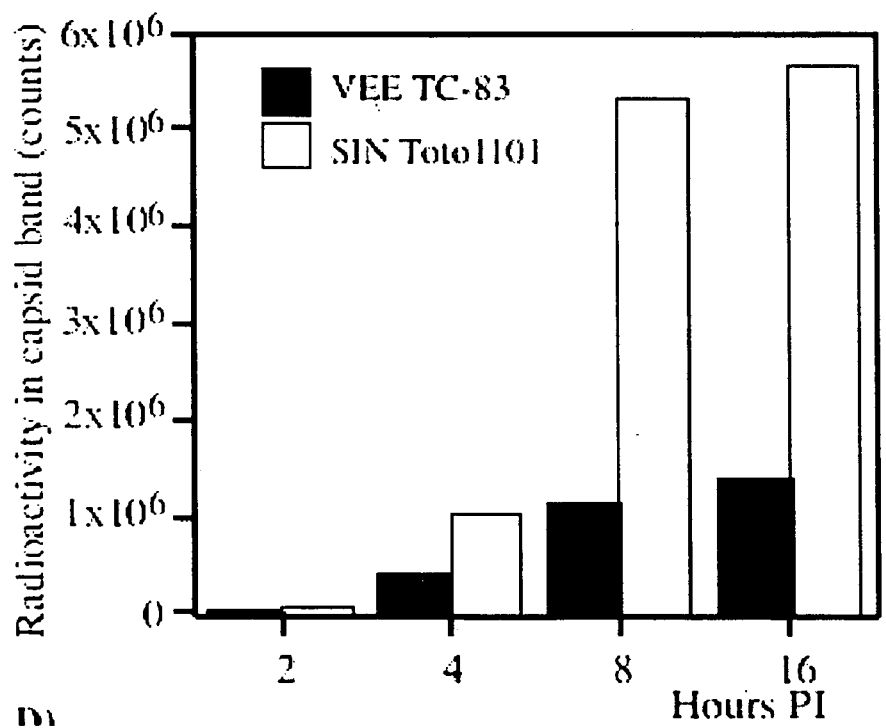
Figure 14C:
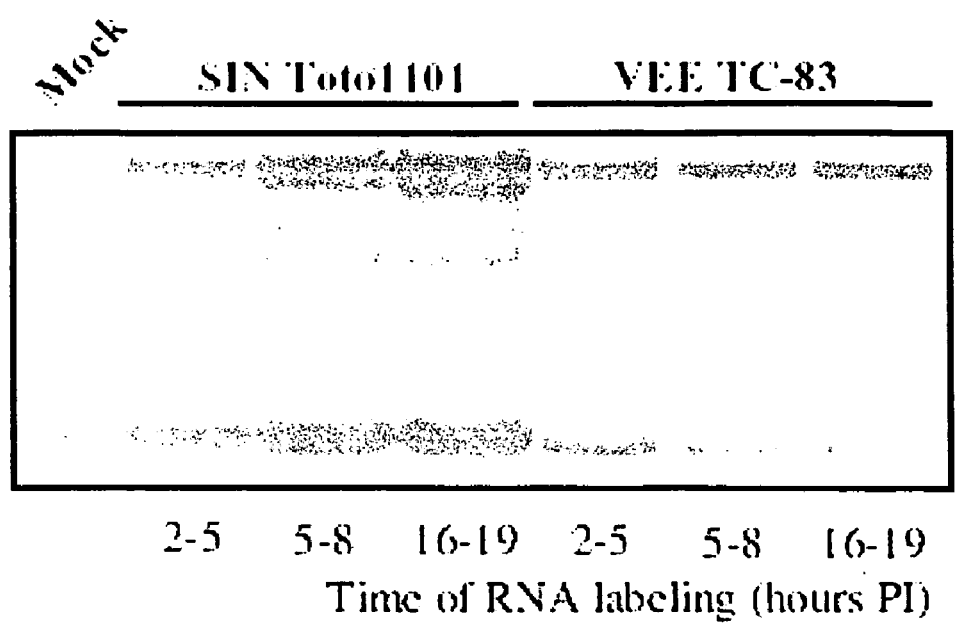
Figure 14D:
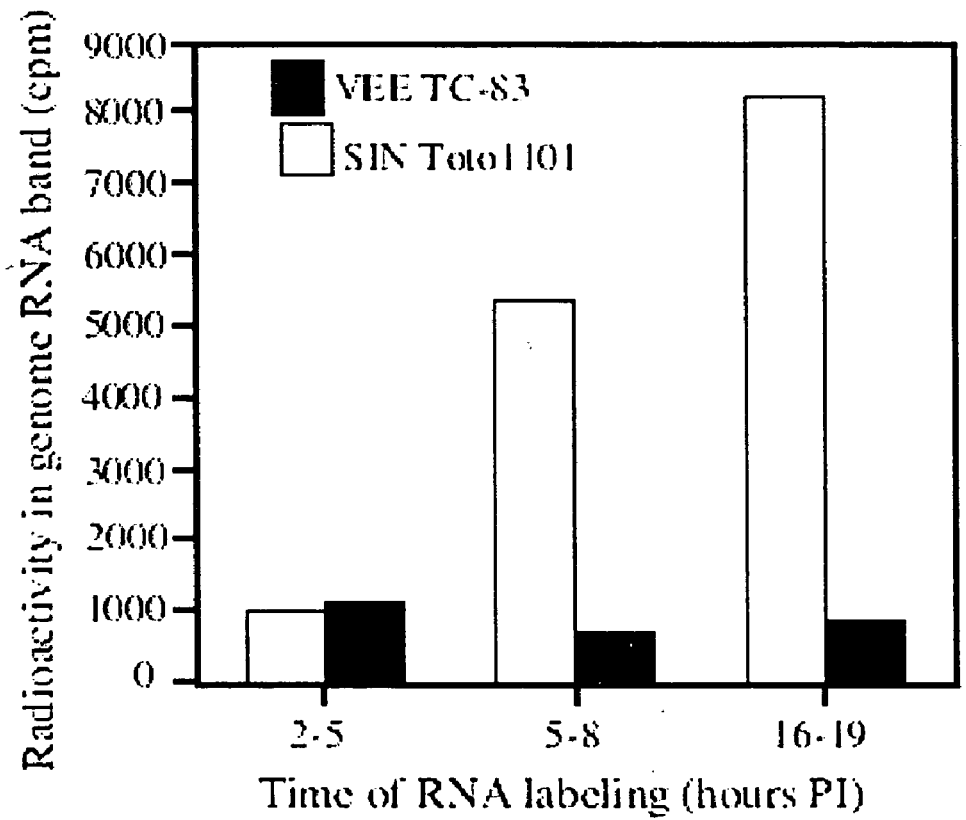
Figure 14E:
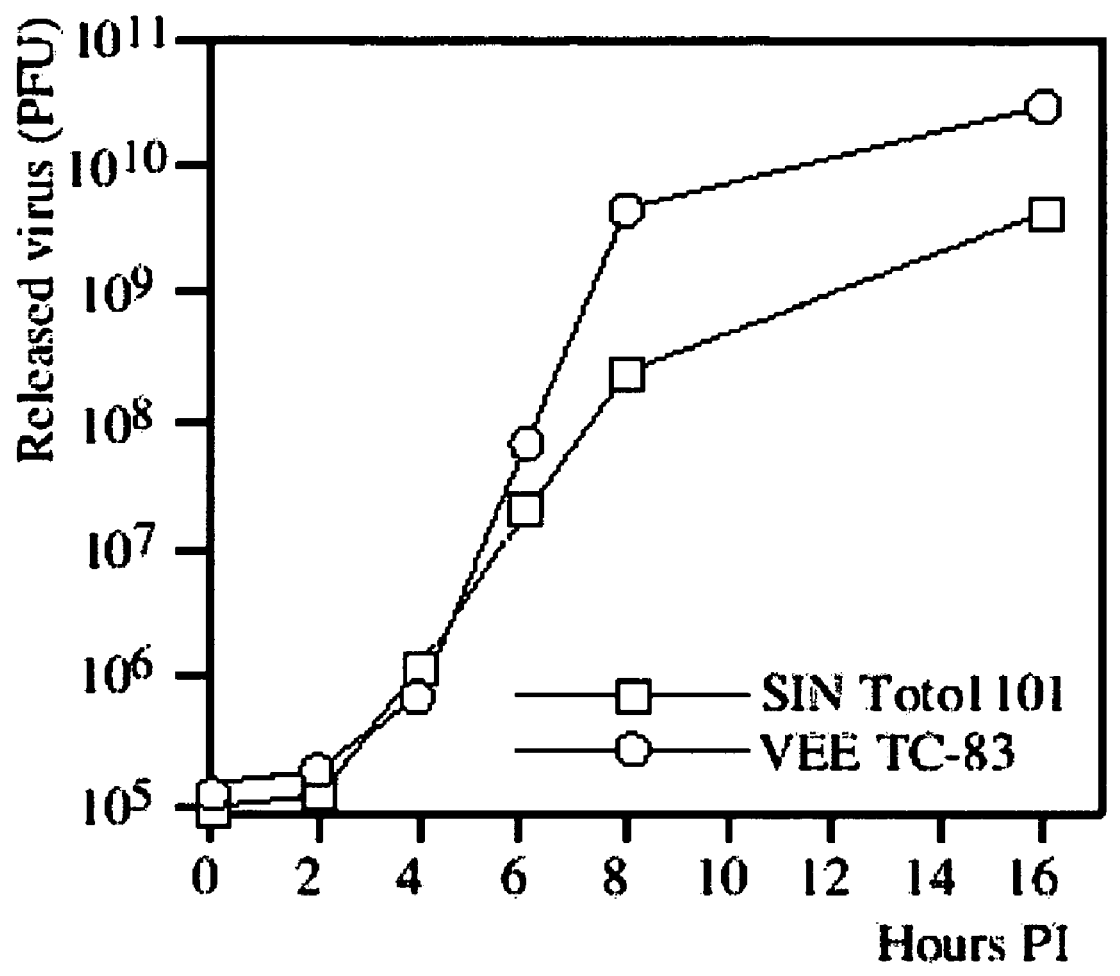

To further investigate the specific characteristics of VEE packaging, BHK-21 cells were infected with VEE TC-83 and virus release, synthesis of virus-specific RNAs and viral structural proteins with those in SIN Toto1101-infected cells was compared. At any time post infection, at an MOI 10 PFU/cell, VEE-specific structural proteins were synthesized 5-6-fold less efficiently than were those SIN-specific proteins (FIG. 14A-14B). VEE RNA replication and transcription of the subgenomic RNAs were also 7- to 8-fold lower compared to the levels found in SIN-infected cells (FIG. 14C-14D). VEE TC-83 virus was used in these experiments for safety reasons, but note that it has been demonstrated herein that $A_3G$ mutation does not change the level of genome RNA replication). However, in contrast to more efficient production of both RNA and protein components of the virions, infectious SIN virus particles were released to the media at almost 50-fold lower rates, starting from as early as 4 h post infection, and accumulated to a 10- to 20-fold lower final concentration.

One of the possible explanations for such strong disagreement between infectious virus release and the rates of viral proteins and RNA synthesis could be due to the lower infectivity of SIN virions. To rule out this possibility, freshly prepared stocks of VEE TC-83 and SIN Toto1101 viruses were purified to homogeneity on sucrose gradients. VEE TC-83 samples demonstrated a specific infectivity of 2.8-4.2×10$^9$ PFU/μg of protein. SIN Toto1101 infectivity was found to be 3- to 4-fold lower, namely, 0.97-1.5×10$^9$ PFU/μg of protein. However, the observed 3-to 4-fold difference in the infectivities could not explain the strong discrepancy between lower protein and RNA synthesis in the VEE-infected cells and higher titers of the released infectious virus. Thus, VEE appears to use a more efficient mechanism(s) of virus particle formation that leads to higher levels of virus replication in spite of the less efficient synthesis of the structural proteins and virus-specific RNAs.

The following references are cited herein.

1. Griffin, D. E. 2001. Alphaviruses, p. 917-962. In D. M. Knipe and P. M. Howley (ed.), Fields virology, 4th ed. Lippincott, Williams and Wilkins, New York, N.Y.
2. Strauss, J. H., and Strauss, E. G. 1994. Microbiol. Rev. 58:491-562.
3. Weaver, S. C. and Barrett, A. D. 2004. Nat. Rev. Microbiol. 2:789-801.
4. Strauss, et al. 1984. Virology 133:92-110.
5. Kinney, et al. 1993. J. Virol. 67:1269-1277.
6. Takkinen, K. 1986. Nucleic Acids Res. 14:5667-5682.
7. Berge, et al. 1961. Am. J. Hyg. 73:209-218.
8. Frolov, et al. 1999. J. Virol. 73:3854-3865.
9. Rice, et al. 1987. J. Virol. 61:3809-3819.
10. Bredenbeek, et al. 1993. J. Virol. 67, 6439-6446.
11. Fayzulin, et al. 2005. J Virol 79(1), 637-43.
12. Liljeström, et al. 1991. J. Virol.65:4107-4113.
13. Lemm, et al. 1990. J. Virol. 64:3001-3011.
14. White, et al. 2001. J. Virol. 75:3706-3718.
15. Liljeström, P. and Garoff, H. 1991. BioTechnology 9:1356-1361.
16. Lundstrom, et al. 2003. Mol. Ther. 7:202-209.
17. Lundstrom, et al. 1999. Gene Ther. Mol. Biol. 4:23-31.
18. Perri, et al. 2000. J. Virol. 74:9802-9807.
19. Frolov, I., and Schlesinger, S. (1996). J. Virol. 70(2), 1182-90.
20. Spotts, et al. 1998. J. Virol. 72:10286-10291.
21. Johnston, et al. 1974. J. Virol. 14:1076-1082.
22. Agapov, et al. 1998. Proc. Natl. Acad. Sci. USA 95:12989-12994.
23. Frolova, et al. 2002. J. Virol. 76:11254-11264.
24. Dryga, et al. 1997. Virology 228:72-83.
25. Kinney, et al. 1989. Virology 170, 19-30.
26. Gorchakov, et al. 2004. J Virol 78(16), 8455-67.
27. Liljeström, P. and Garoff, H. 1991. BioTechnology 9, 1356-1361.
28. Pushko, et al. 1997. Virology 239(2), 389-401.
29. Frolova, et al. 1997. J Virol 71(1), 248-58.
30. Lehtovaara, et al. 1982. J. Mol. Biol. 156, 731-748.
31. Monroe, S. S. and Schlesinger, S. 1983. Proc. Natl. Acad. Sci. USA 80(11), 3279-3283.
32. Monroe, S. S. and Schlesinger, S. 1984. J. Virol. 49, 865-872.
33. White, et al. 1998. J Virol 72(5), 4320-6.
34. Geigenmuller-Gnirke, et al. 1991. Proc. Natl. Acad. Sci. USA 88, 3253-3257.

Any publications mentioned in this specification are indicative of the levels of those skilled in the art to which the invention pertains. Further, these publications are incorporated by reference herein to the same extent as if each individual publication was specifically and individually incorporated by reference.

The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A Venezuelan equine encephalitis virus replicon RNA, wherein said replicon RNA in a 5' to 3' order comprises: a 5' sequence required for nonstructural protein-mediated amplification; a nucleotide sequence encoding nonstructural proteins nsP1, nsP2, nsP3, and nsP4 of the Venezuelan equine encephalitis virus, wherein said nucleotide sequence encodes one or more of a adaptive mutation(s) nsP2Q739L, nsP2P773S or nsP3L121P; one or more promoters each of which is operably linked to one or more heterologous nucleic acid sequence(s) encoding heterologous protein(s) that replaces one or all of the Venezuelan equine encephalitis virus structural protein genes; a 3' sequence required for nonstructural protein-mediated amplification; and a poly-adenylate tract, wherein the third nucleotide in the 5' UTR of the replicon is a guanine such that the presence of the guanine as the third nucleotide in the 5'UTR of the replicon and the adaptive mutation(s) are effective in reducing the cytopathogenicity of the replicon upon cellular infection.

2. The replicon RNA of claim 1, wherein one of said heterologous proteins is a selection marker.

3. The replicon RNA of claim 2, wherein said selection marker is a fluorescent protein, puromycin acetyltransferase, or neomycin acetyltransferase.

4. A cDNA copy of the replicon of claim 1, wherein said cDNA has a 5' promoter that directs synthesis of alphavirus RNA in vivo from cDNA.

5. The cDNA of claim 4, wherein said 5' promoter is a eukaryotic RNA polymerase II promoter.

6. An alphavirus particle comprising the replicon RNA of claim 1.

7. An isolated cell comprising the replicon of claim 1.

8. The cell of claim 7, wherein said cell is a mammalian cell, an insect cell, or an avian cell.

9. The cell of claim 7, wherein said cell secretes or responds to interferon.

10. A method of expressing one or more heterologous proteins in a cell, comprising:
   introducing the replicon RNA of claim 1 into a cell; and
   expressing the heterologous protein encoded by said replicon in the cell.

11. The method of claim 10, wherein said replicon RNA is introduced into said cell by infection or transfection.

12. The method of claim 10, wherein said cell secretes or responds to interferon.

13. A method of screening for an inhibitory compound of Venezuelan equine encephalitis virus replication, comprising:
   introducing into a cell the replicon RNA of claim 1; and
   measuring the level of replication of said replicon in the presence or absence of said inhibitory compound, wherein a decreased level of production of heterologous marker protein encoded by the replicon correlates with a lower level of replicon replication in the presence of the inhibitory compound; said lower level of replicon replication in the presence of the inhibitory compound indicating that said inhibitory compound would inhibit replication of Venezuelan equine encephalitis virus.

14. The method of claim 13, wherein said replicon RNA is introduced into said cell by infection or transfection.

15. The method of claim 13, wherein said cell is capable of secreting or responding to interferon.

* * * * *

```
                              SEQUENCE LISTING

<160> NUMBER OF SEQ ID NOS: 10

<210> SEQ ID NO 1
<211> LENGTH: 13
<212> TYPE: DNA
<213> ORGANISM: artificial sequence
<220> FEATURE:
<223> OTHER INFORMATION: a synthetic nucleotide sequence found in a
      puromycin acetyltransferase-encoding cassette

<400> SEQUENCE: 1
tctagagctt acc                                                          13

<210> SEQ ID NO 2
<211> LENGTH: 11
<212> TYPE: DNA
<213> ORGANISM: artificial sequence
<220> FEATURE:
<223> OTHER INFORMATION: a synthetic nucleotide sequence found in a
      secreted alkaline phosphatase-encoding cassette

<400> SEQUENCE: 2
tctaggtgag c                                                            11

<210> SEQ ID NO 3
<211> LENGTH: 69
<212> TYPE: PRT
<213> ORGANISM: artificial sequence
<220> FEATURE:
<222> LOCATION: 707..775
<223> OTHER INFORMATION: partial coding sequence of nsP2 in VEE replicon
      with adaptive mutations at positions 708, 713, 739,
      and 773 and a deletion between 765 and 766

<400> SEQUENCE: 3

Ala Cys Leu His Leu Asn Pro Gly Gly Thr Cys Val Ser Ile Gly
                 5                  10                  15

Tyr Gly Tyr Ala Asp Arg Ala Ser Glu Ser Ile Ile Gly Ala Ile
             20                  25                  30

Ala Arg Gln Phe Lys Phe Ser Arg Val Cys Lys Pro Lys Ser Ser
             35                  40                  45

Leu Glu Glu Thr Glu Val Leu Phe Val Phe Ile Gly Tyr Asp Arg
             50                  55                  60

Lys Ala Arg Thr His Asn Pro Tyr Lys
                 65

<210> SEQ ID NO 4
<211> LENGTH: 70
<212> TYPE: PRT
<213> ORGANISM: Alphavirus
<220> FEATURE:
<223> OTHER INFORMATION: homologous sequence of eastern equine
      encephalitis virus to partial nsP3 coding sequence in VEE
      replicon at 707 to 775

<400> SEQUENCE: 4

Ala Val Asp His Leu Asn Lys Gly Gly Thr Cys Ile Ala Leu Gly
                 5                  10                  15
```

Tyr Gly Thr Ala Asp Arg Ala Thr Glu Asn Ile Ile Ser Ala Val
                20                  25                  30

Ala Arg Ser Phe Arg Phe Ser Arg Val Cys Gln Pro Lys Cys Ala
                35                  40                  45

Trp Glu Asn Thr Glu Val Ala Phe Val Phe Phe Gly Lys Asp Asn
                50                  55                  60

Gly Asn His Leu Ala Asp Gln Asp Arg Leu
                65                  70

<210> SEQ ID NO 5
<211> LENGTH: 70
<212> TYPE: PRT
<213> ORGANISM: Alphavirus
<220> FEATURE:
<223> OTHER INFORMATION: homologous sequence of Sindbis virus to partial
      nsP3 coding sequence in VEE replicon at 707 to 775

<400> SEQUENCE: 5

Ala Leu Asn Cys Leu Asn Pro Gly Gly Thr Leu Val Val Lys Ser
                 5                  10                  15

Tyr Gly Tyr Ala Asp Arg Asn Ser Glu Asp Val Val Thr Ala Leu
                20                  25                  30

Ala Arg Lys Phe Val Arg Val Ser Ala Ala Arg Pro Asp Cys Val
                35                  40                  45

Ser Ser Asn Thr Glu Met Tyr Leu Ile Phe Arg Gln Leu Asp Asn
                50                  55                  60

Ser Arg Thr Arg Gln Phe Thr Pro His His
                65                  70

<210> SEQ ID NO 6
<211> LENGTH: 68
<212> TYPE: PRT
<213> ORGANISM: Alphavirus
<220> FEATURE:
<223> OTHER INFORMATION: homologous sequence of Semliki Forest virus to
      partial nsP3 coding sequence in VEE replicon
      at 707 to 775

<400> SEQUENCE: 6

Ala Leu Arg Leu Leu Asp Pro Gly Gly Ile Leu Met Arg Ala Tyr
                 5                  10                  15

Gly Tyr Ala Asp Lys Ile Ser Glu Ala Val Val Ser Ser Leu Ser
                20                  25                  30

Arg Lys Phe Ser Ser Ala Arg Val Leu Arg Pro Asp Cys Val Thr
                35                  40                  45

Ser Asn Thr Glu Val Phe Leu Leu Phe Ser Asn Phe Asp Asn Gly
                50                  55                  60

Lys Arg Pro Ser Thr Leu His Gln
                65

<210> SEQ ID NO 7
<211> LENGTH: 23
<212> TYPE: PRT
<213> ORGANISM: Alphavirus
<220> FEATURE:
<222> LOCATION: 108..130
<223> OTHER INFORMATION: partial coding sequence of nsP3 in VEE replicon
      with adaptive mutations at position 121

<400> SEQUENCE: 7

Leu Leu Ser Thr Gly Ile Phe Ser Gly Asn Lys Asp Arg Leu Thr
                 5                  10                  15

```
Gln Ser Leu Asn His Leu Leu Thr
                20

<210> SEQ ID NO 8
<211> LENGTH: 23
<212> TYPE: PRT
<213> ORGANISM: Alphavirus
<220> FEATURE:
<223> OTHER INFORMATION: homologous sequence of eastern equine
      encephalitis virus to partial nsP3 coding sequence in VEE
      replicon at 108 to 130

<400> SEQUENCE: 8

Leu Leu Ser Thr Gly Ile Tyr Ala Gly Gly Lys Asp Arg Val Met
                5                   10                  15

Gln Ser Leu Asn His Leu Phe Thr
                20

<210> SEQ ID NO 9
<211> LENGTH: 23
<212> TYPE: PRT
<213> ORGANISM: Alphavirus
<220> FEATURE:
<223> OTHER INFORMATION: homologous sequence of Sindbis virus to partial
      nsP3 coding sequence in VEE replicon at 108 to 130

<400> SEQUENCE: 9

Leu Leu Ser Thr Gly Ile Tyr Ala Ala Gly Lys Asp Arg Leu Glu
                5                   10                  15

Val Ser Leu Asn Cys Leu Thr Thr
                20

<210> SEQ ID NO 10
<211> LENGTH: 23
<212> TYPE: PRT
<213> ORGANISM: Alphavirus
<220> FEATURE:
<223> OTHER INFORMATION: homologous sequence of Semliki Forest virus to
      partial nsP3 coding sequence in VEE replicon
      at 108 to 130

<400> SEQUENCE: 10

Leu Leu Ser Thr Gly Val Phe Ser Gly Gly Arg Asp Arg Leu Gln
                5                   10                  15

Gln Ser Leu Asn His Leu Phe Thr
                20
```